(12) United States Patent
Kumar et al.

(10) Patent No.: US 9,492,406 B2
(45) Date of Patent: Nov. 15, 2016

(54) PHARMACEUTICAL COMPOSITION

(71) Applicant: IPCA Laboratories Limited, Mumbai, Maharashtra (IN)

(72) Inventors: Ashok Kumar, Maharashtra (IN); Dharmendra Singh, Maharashtra (IN); Pramilkumar Mathur, Maharashtra (IN); Thankachen Byju Nellithanath, Maharashtra (IN); Gaurav Sahal, Maharashtra (IN); Rakesh Kumar Bhasin, Maharashtra (IN); Durga Prasad Samantaray, Maharashtra (IN)

(73) Assignee: Ipca Laboratories Ltd. (IN)

( * ) Notice: Subject to any disclaimer, the term of this patent is extended or adjusted under 35 U.S.C. 154(b) by 0 days.

(21) Appl. No.: 14/430,007

(22) PCT Filed: Sep. 20, 2013

(86) PCT No.: PCT/IN2013/000568
§ 371 (c)(1),
(2) Date: Mar. 20, 2015

(87) PCT Pub. No.: WO2014/045307
PCT Pub. Date: Mar. 27, 2014

(65) Prior Publication Data
US 2015/0238416 A1 Aug. 27, 2015

(30) Foreign Application Priority Data
Sep. 20, 2012 (IN) .......................... 2739/MUM/2012

(51) Int. Cl.
| | | |
|---|---|---|
| *A61K 9/08* | (2006.01) | |
| *A61K 31/55* | (2006.01) | |
| *A61K 31/122* | (2006.01) | |
| *A61K 47/10* | (2006.01) | |
| *A61K 31/155* | (2006.01) | |
| *A61K 9/14* | (2006.01) | |
| *A61K 9/20* | (2006.01) | |
| *A61K 9/48* | (2006.01) | |

(52) U.S. Cl.
CPC ............ *A61K 31/155* (2013.01); *A61K 9/146* (2013.01); *A61K 9/2027* (2013.01); *A61K 9/2077* (2013.01); *A61K 9/4866* (2013.01); *A61K 31/122* (2013.01)

(58) Field of Classification Search
CPC ............ A61K 2300/00; A61K 45/06; A61K 31/5377; A61K 31/4439; A61K 31/4709; A61K 31/122; A61K 31/155; A61K 31/517; A61K 31/137; A61K 31/138; A61K 31/4725; A61K 2039/505; A61K 31/355; A61K 31/506
See application file for complete search history.

(56) References Cited

U.S. PATENT DOCUMENTS

2010/0028425 A1 2/2010 Mehta et al.

FOREIGN PATENT DOCUMENTS

| CA | WO2008/092262 A1 * | 8/2008 |
|---|---|---|
| CN | 101774901 | 7/2010 |
| EP | WO2011/042463 A2 * | 4/2011 |
| EP | WO2011042463 A2 * | 4/2011 |
| WO | WO2011042463 | 4/2011 |

OTHER PUBLICATIONS

International Search Report dated Mar. 29, 2014; International Application No. PCT/IN2013/000568; International Filing Date: Sep. 20, 2013; 4 pages.

* cited by examiner

*Primary Examiner* — Audrea Buckley
(74) *Attorney, Agent, or Firm* — Blank Rome LLP; Brian W. Higgins

(57) ABSTRACT

The present invention relates to a novel pharmaceutical composition having enhanced bioavailability through improved aqueous dissolution of poorly water soluble drugs, and to a method for preparing it. The invention more particularly relates to an oral pharmaceutical composition containing active ingredients of poor aqueous solubility, more specifically, antiparasitic and antipneumocystic drug Atovaquone alone or in combination with Proguanil.

19 Claims, 17 Drawing Sheets

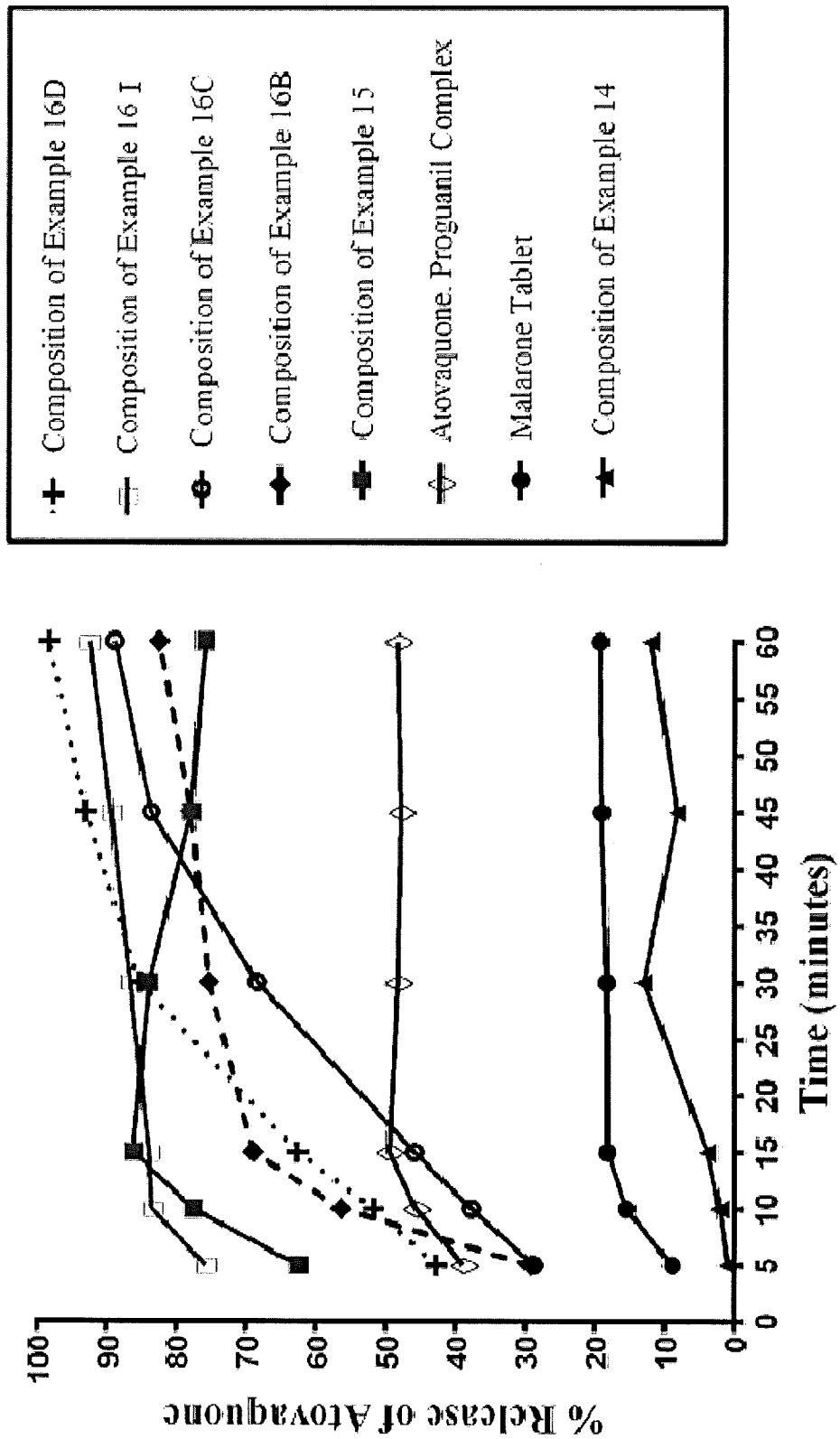
Fig 1(a): Comparative study of the *in vitro* dissolution profile of Atovaquone (in 2.5% w/v SLS in water)

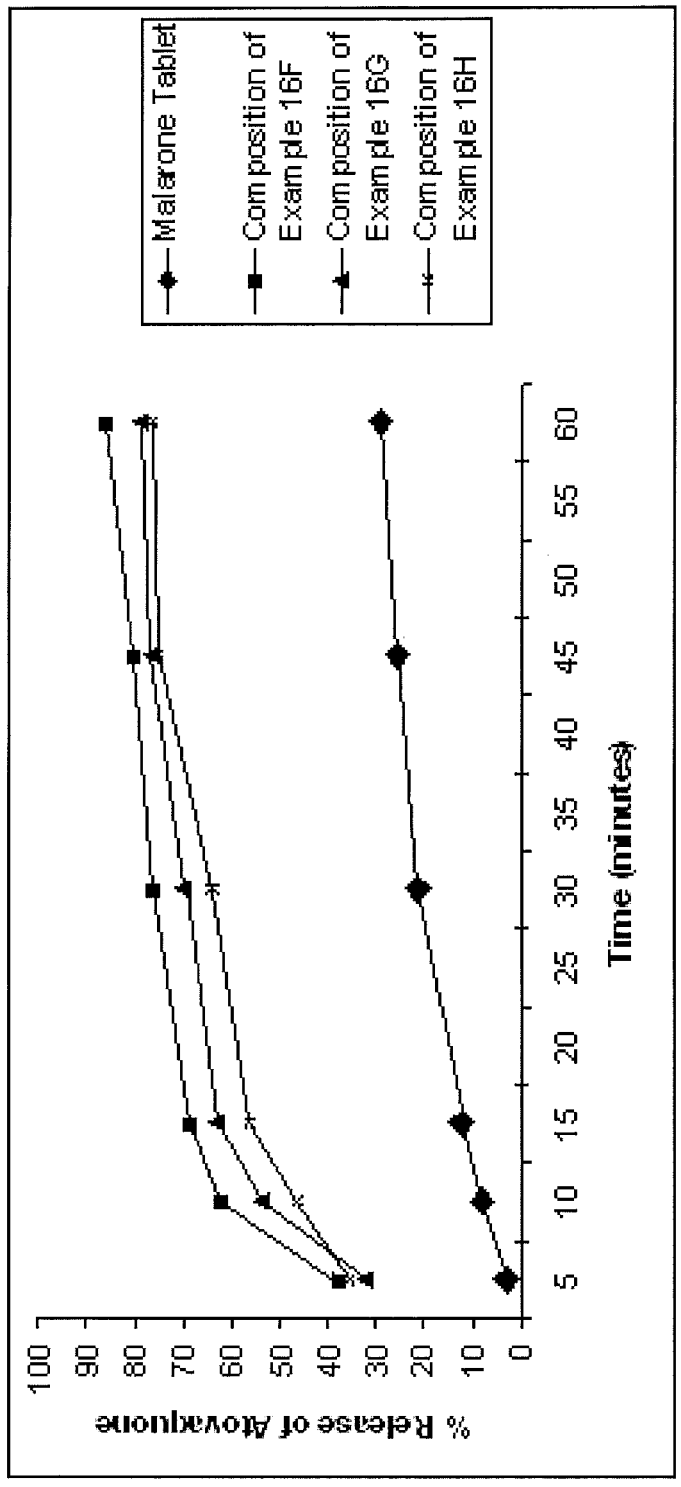
Fig 1(b): Comparative study of the in vitro dissolution profile of Atovaquone (in 2.5% w/v Cremophore EL in water)

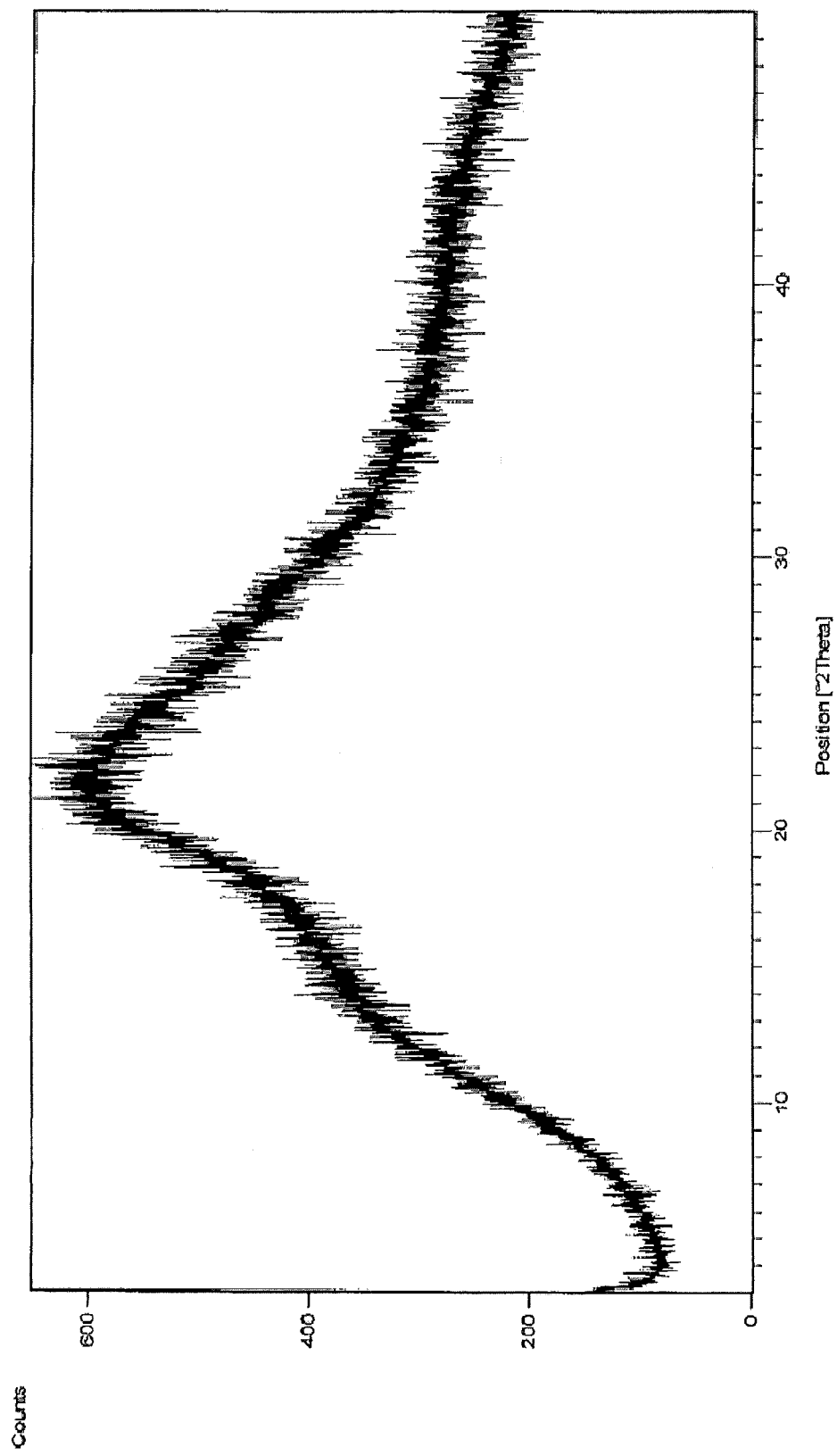
Fig. 2: PXRD pattern of composition of Example 1

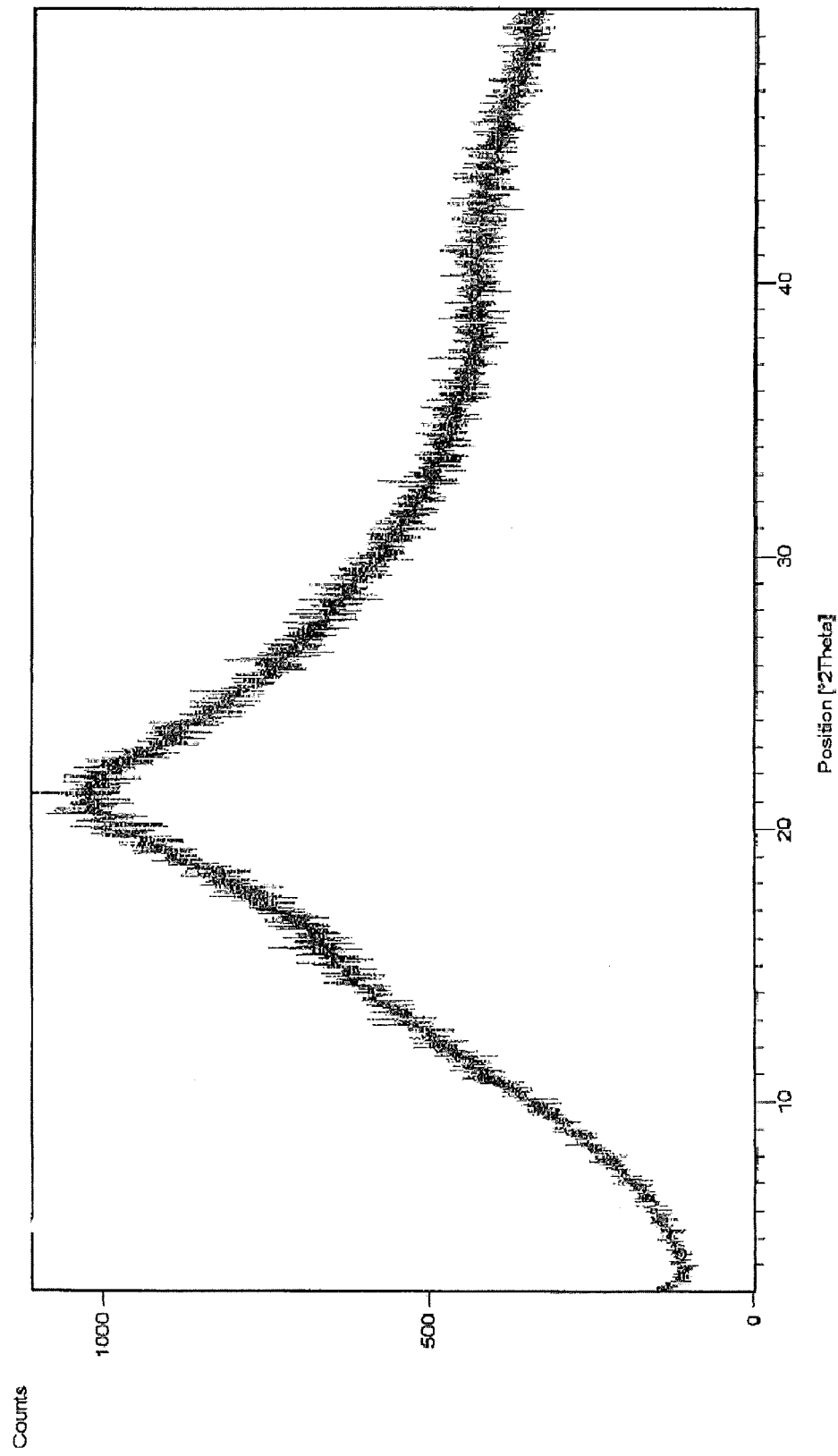
Fig. 3: PXRD pattern of composition of Example 2

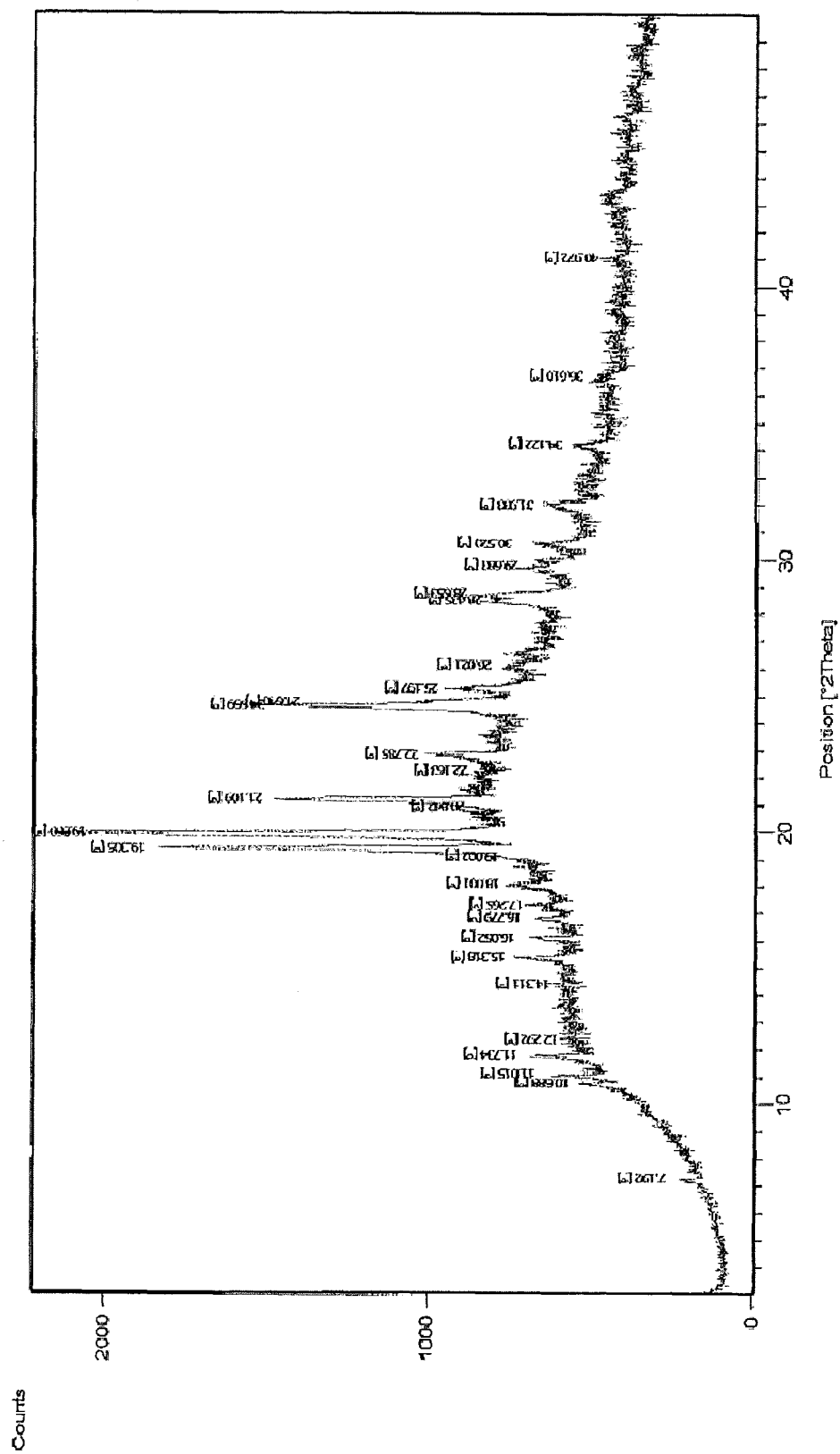
Fig. 4: PXRD pattern of composition of Example 3

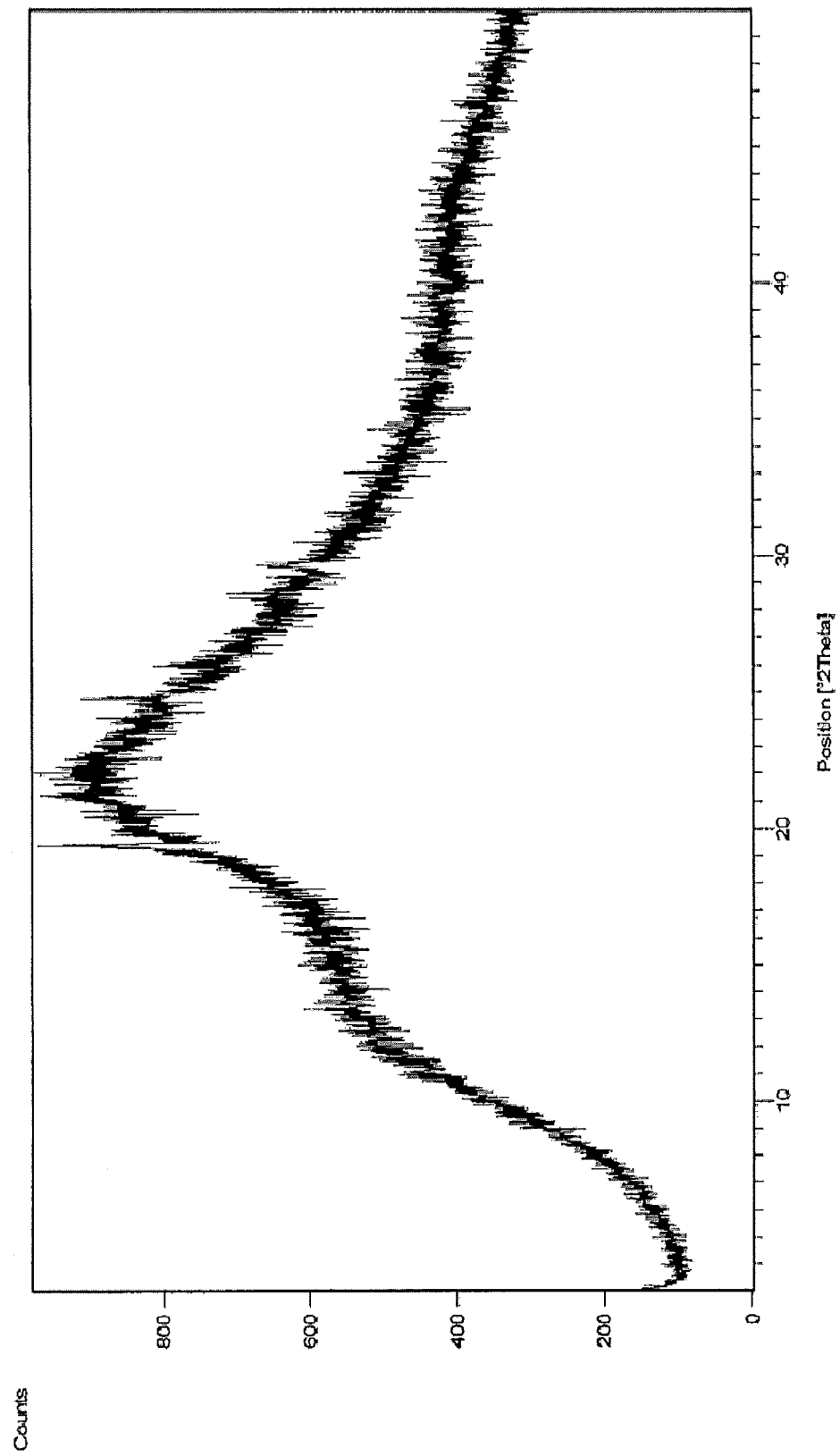
Fig. 5: PXRD pattern of composition of Example 4

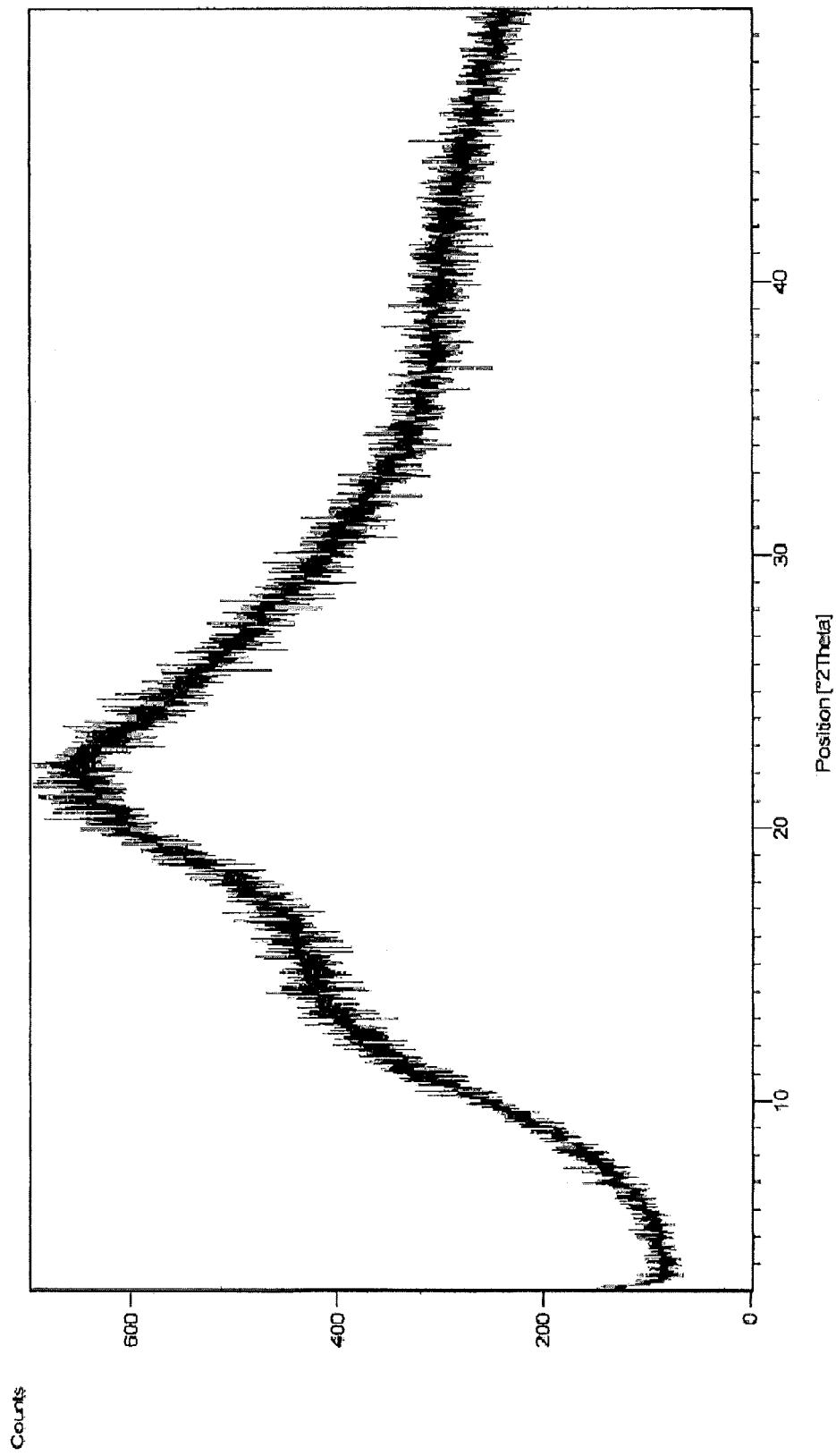
Fig. 6: PXRD pattern of composition of Example 5

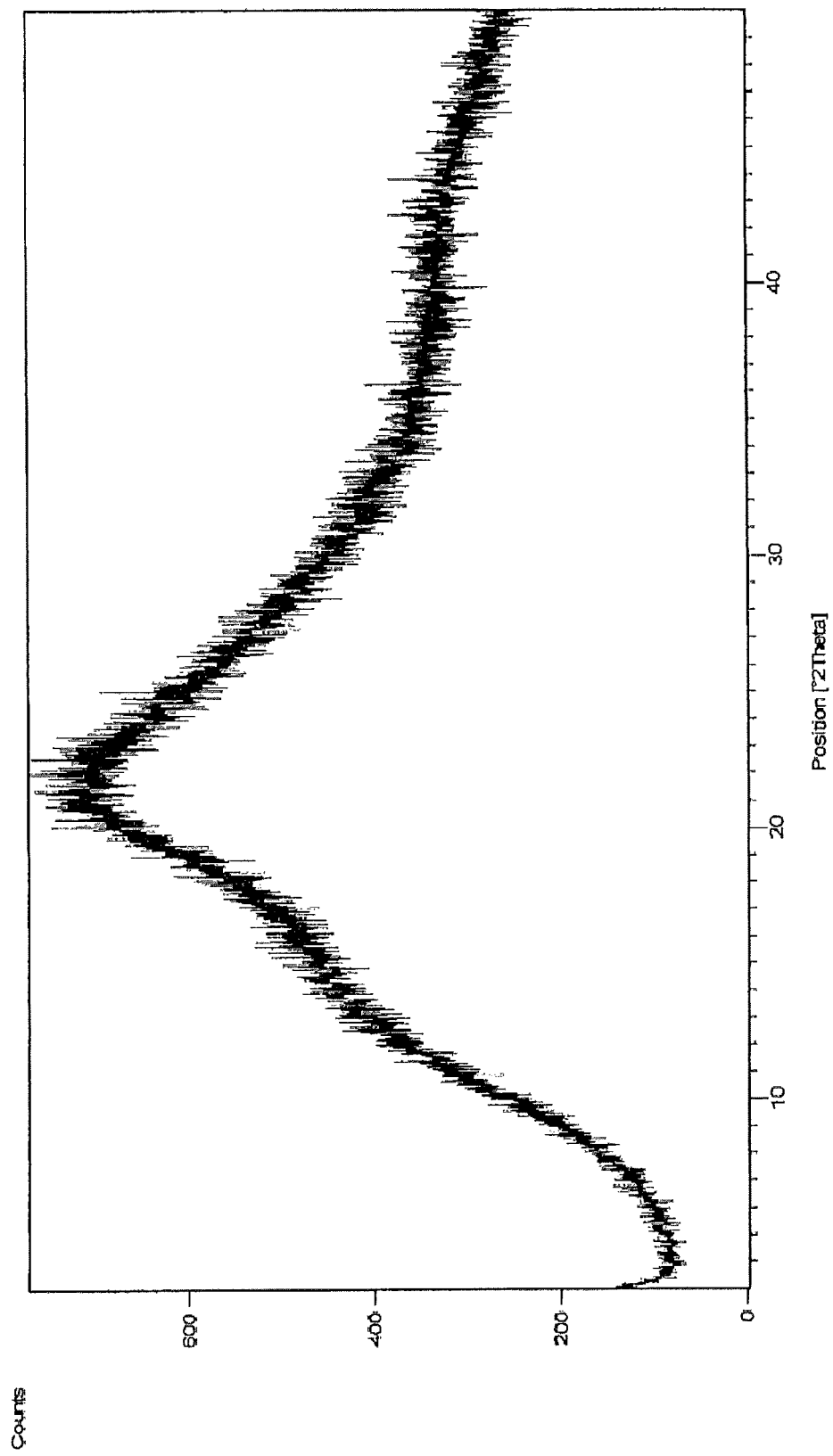
Fig. 7: PXRD pattern of composition of Example 6

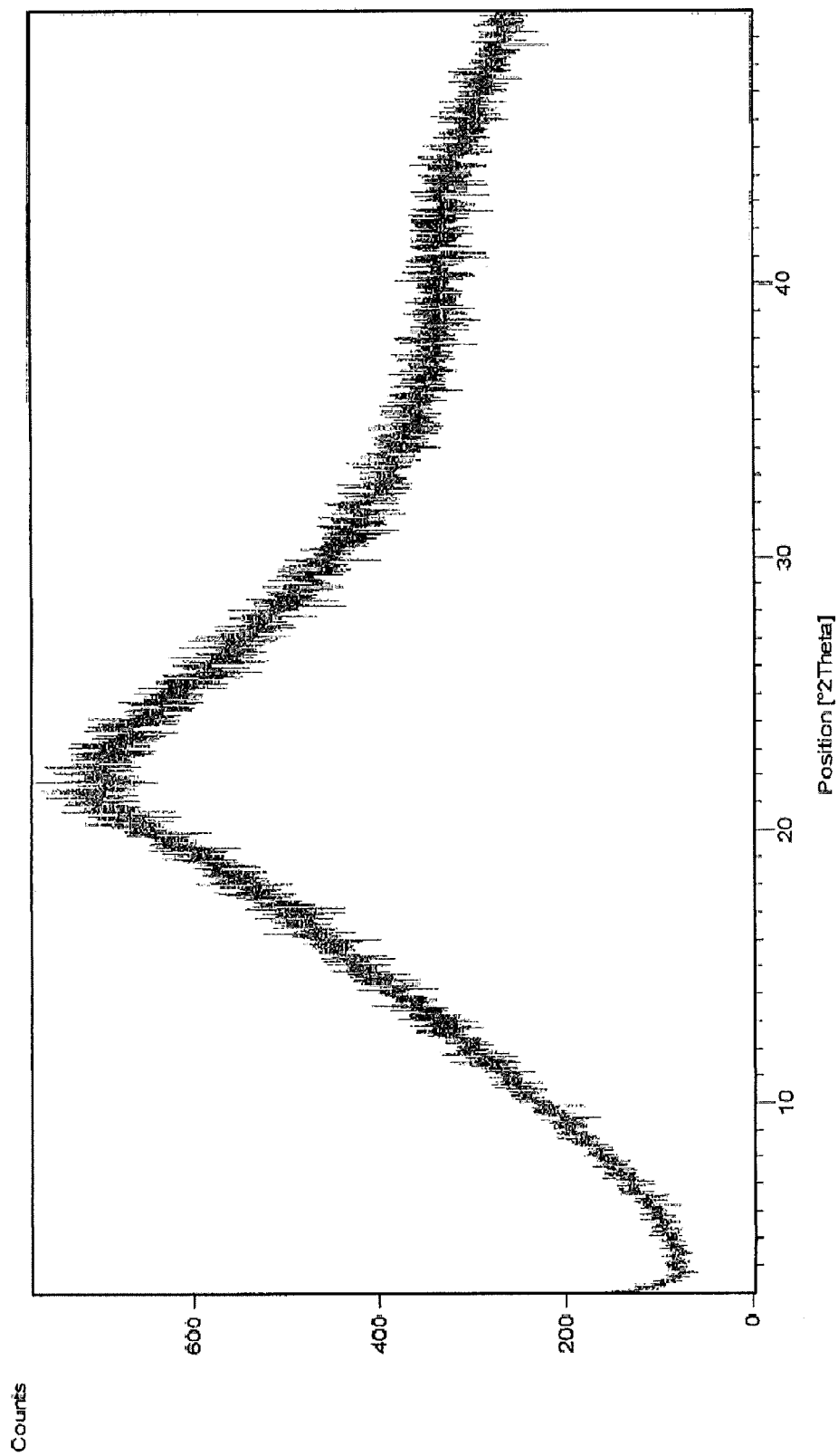
Fig. 8: PXRD pattern of composition of Example 7

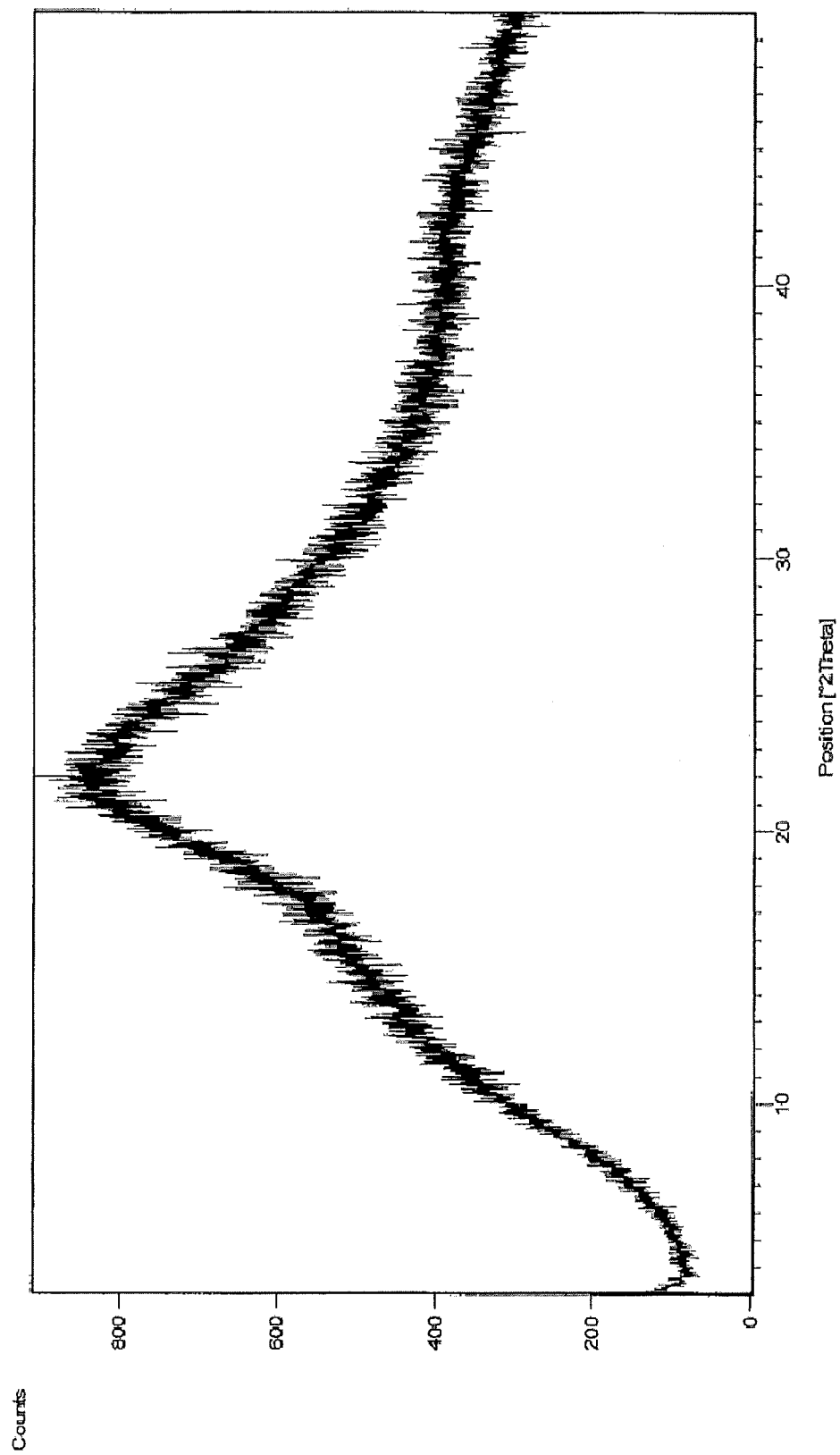
Fig. 9: PXRD pattern of composition of Example 8

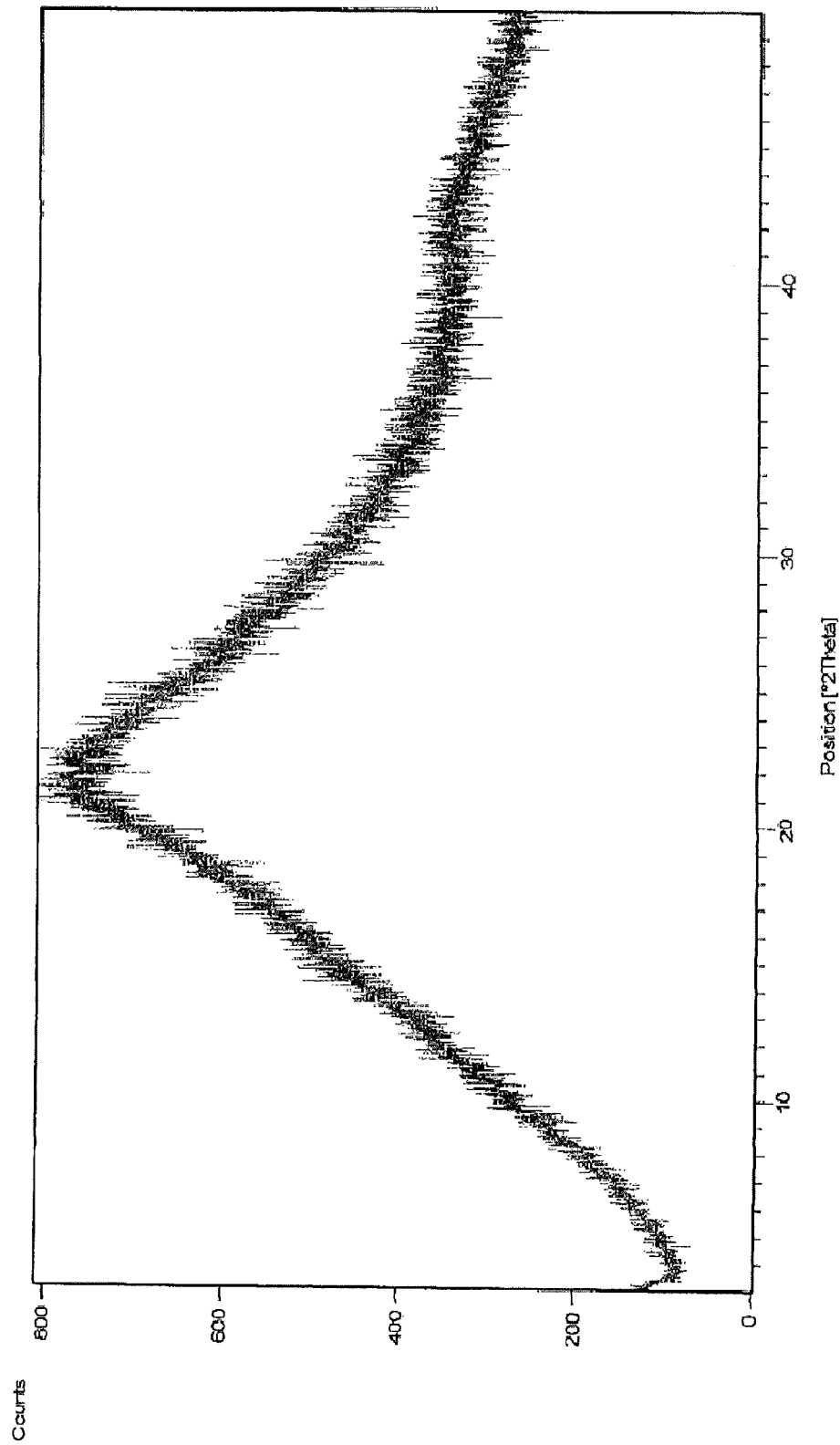

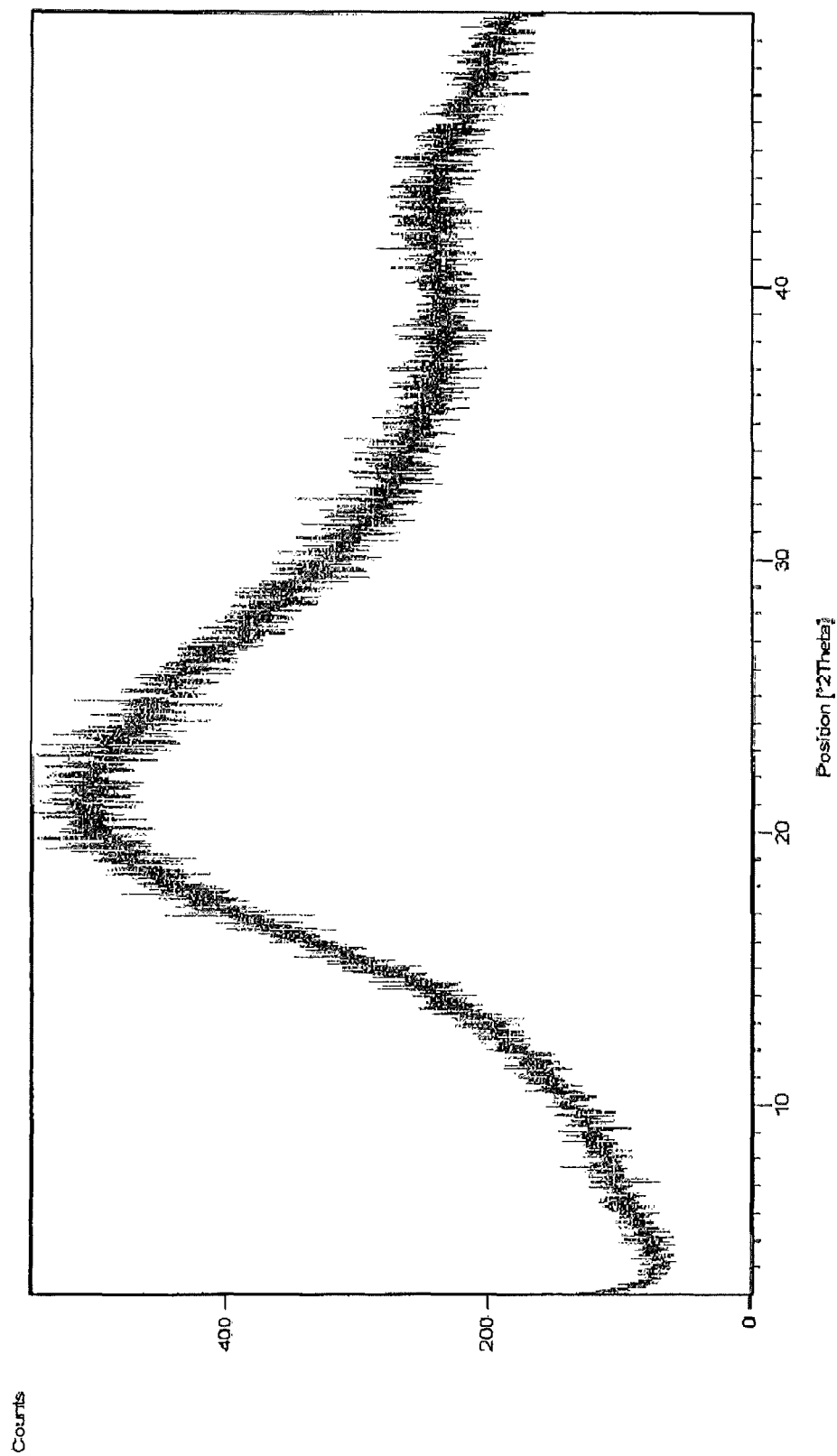
Fig. 11: PXRD pattern of composition of Example 10

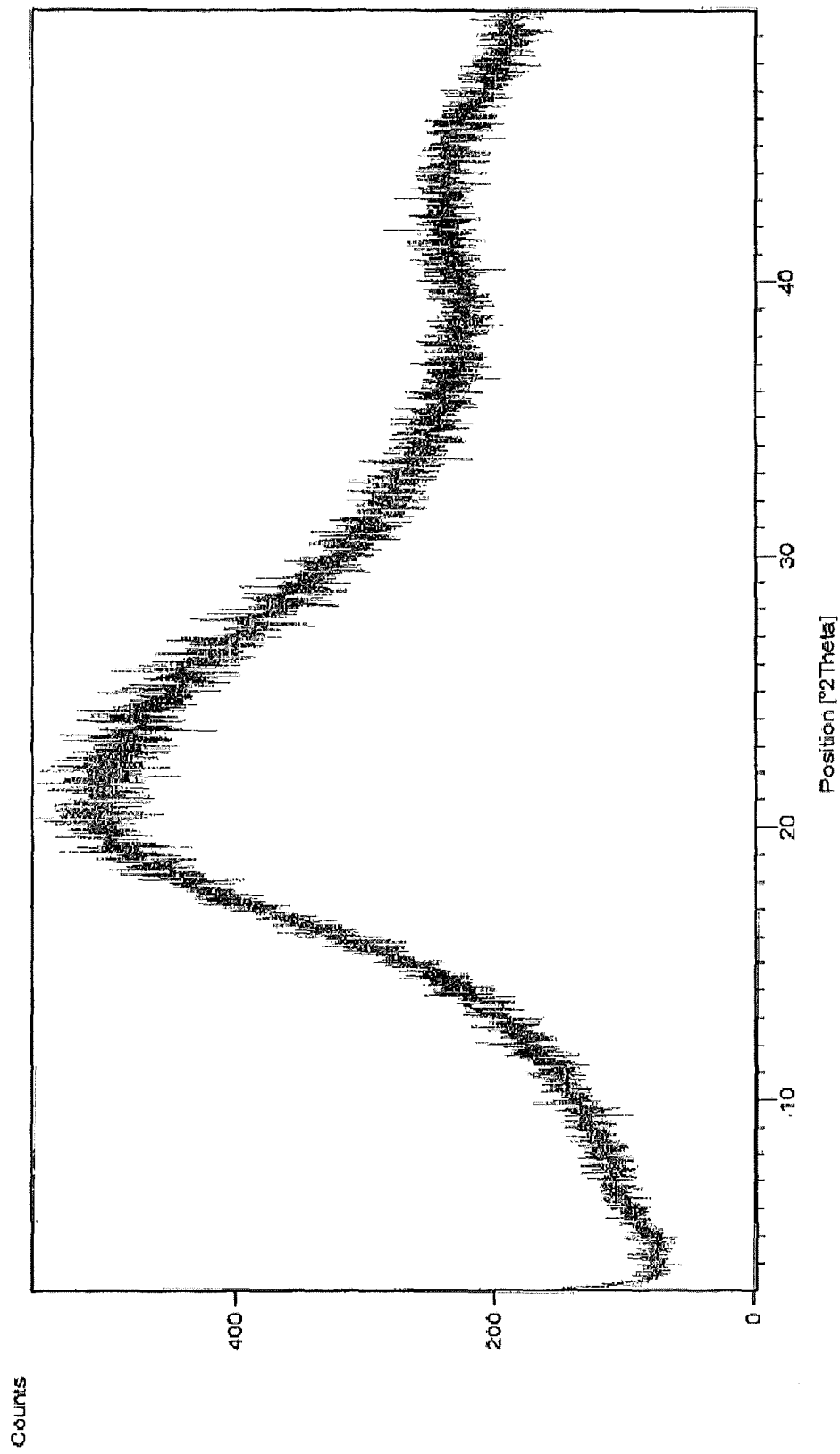
Fig. 12: PXRD pattern of composition of Example 11

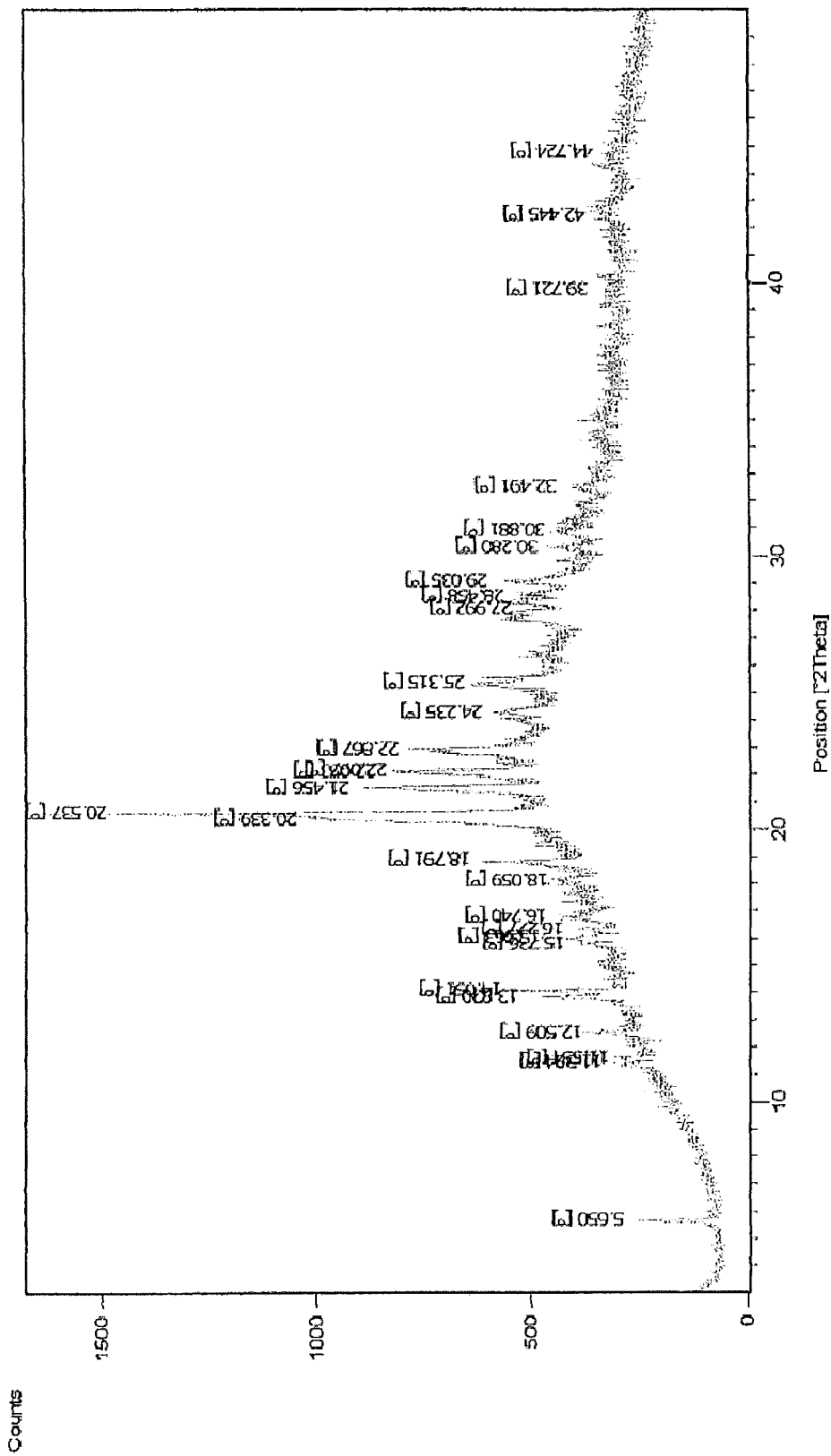
Fig. 13: PXRD pattern of composition of Example 12

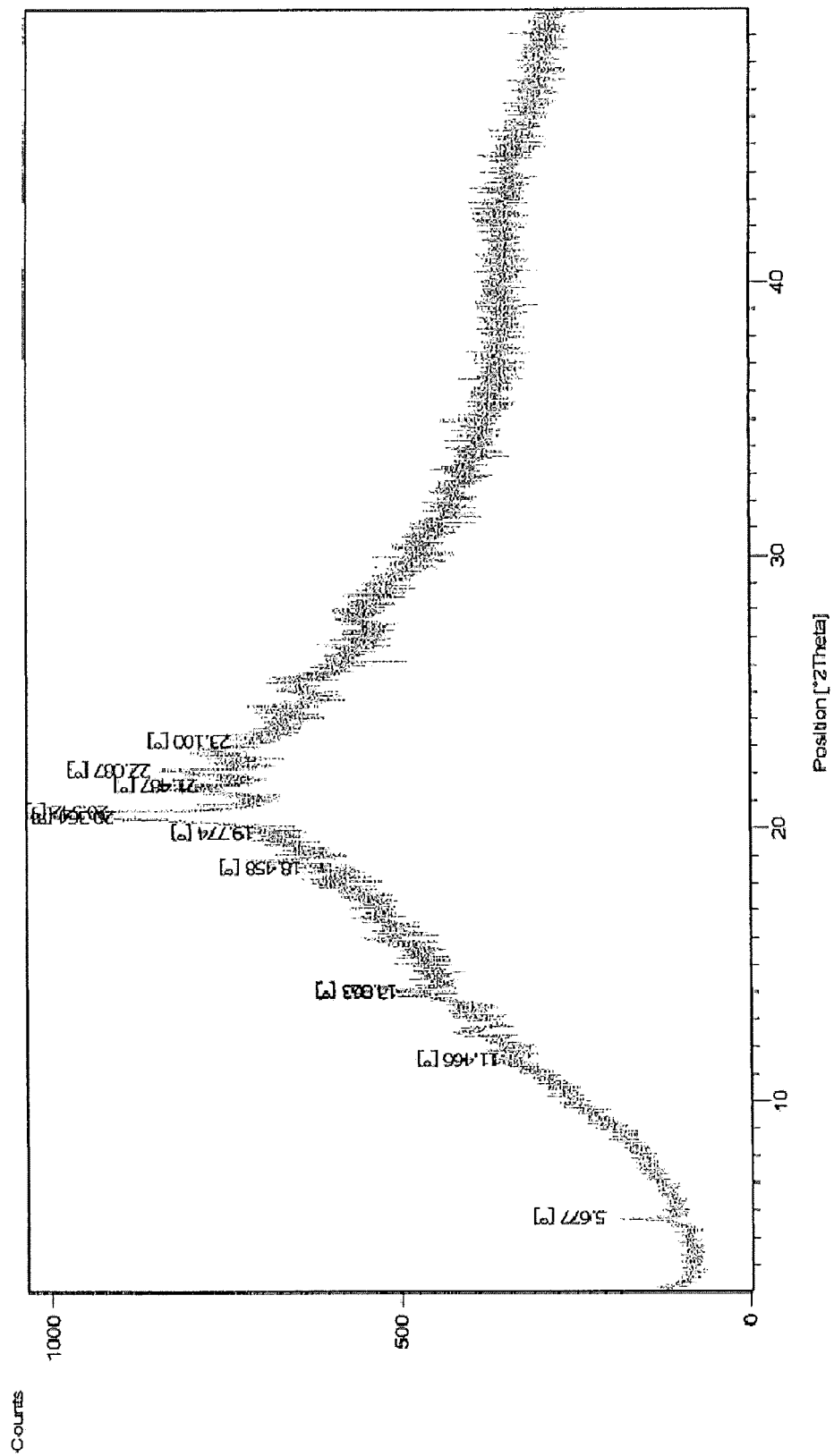
Fig. 14: PXRD pattern of composition of Example 13

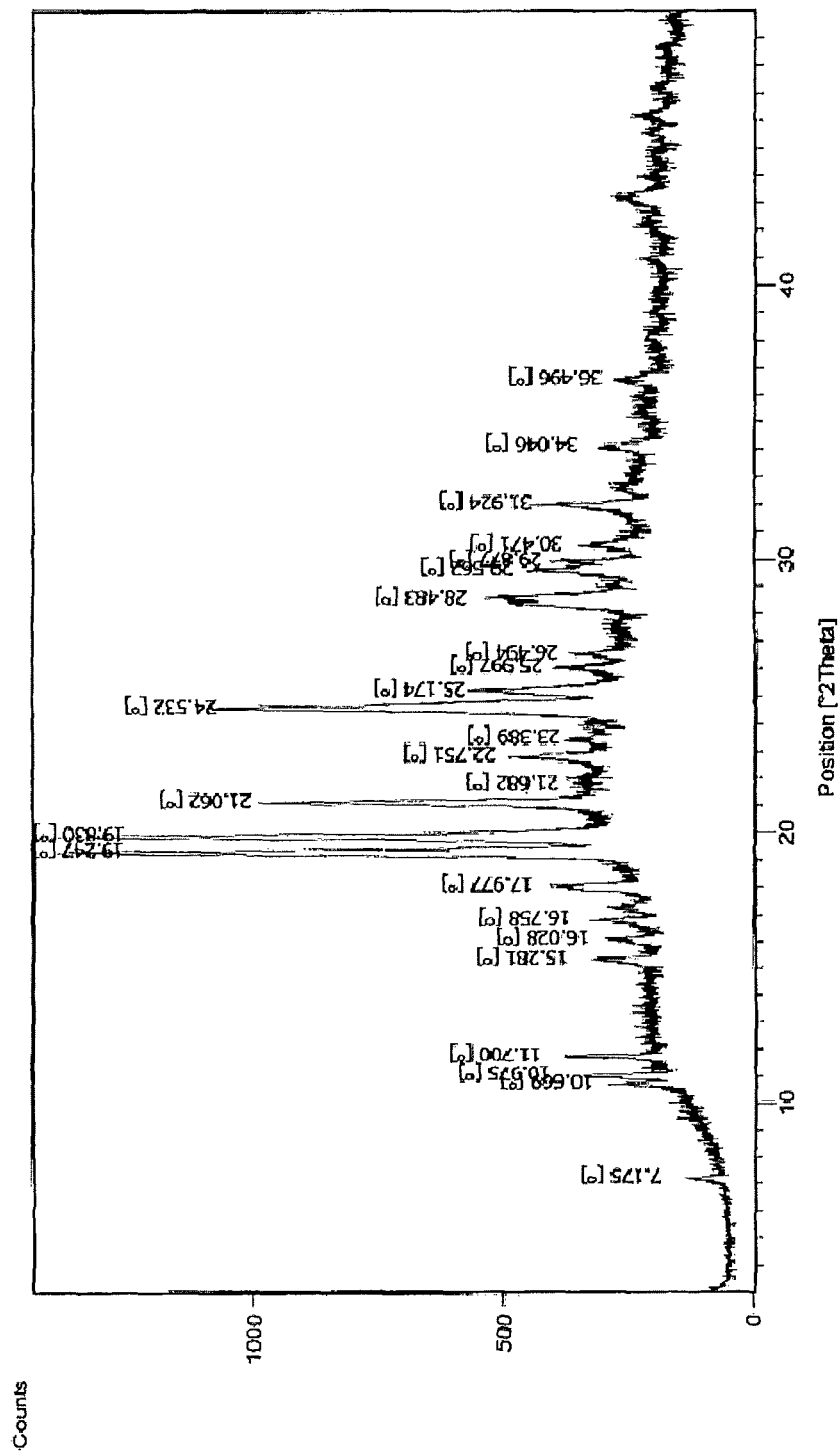
Fig. 15: PXRD pattern of composition of Example 14

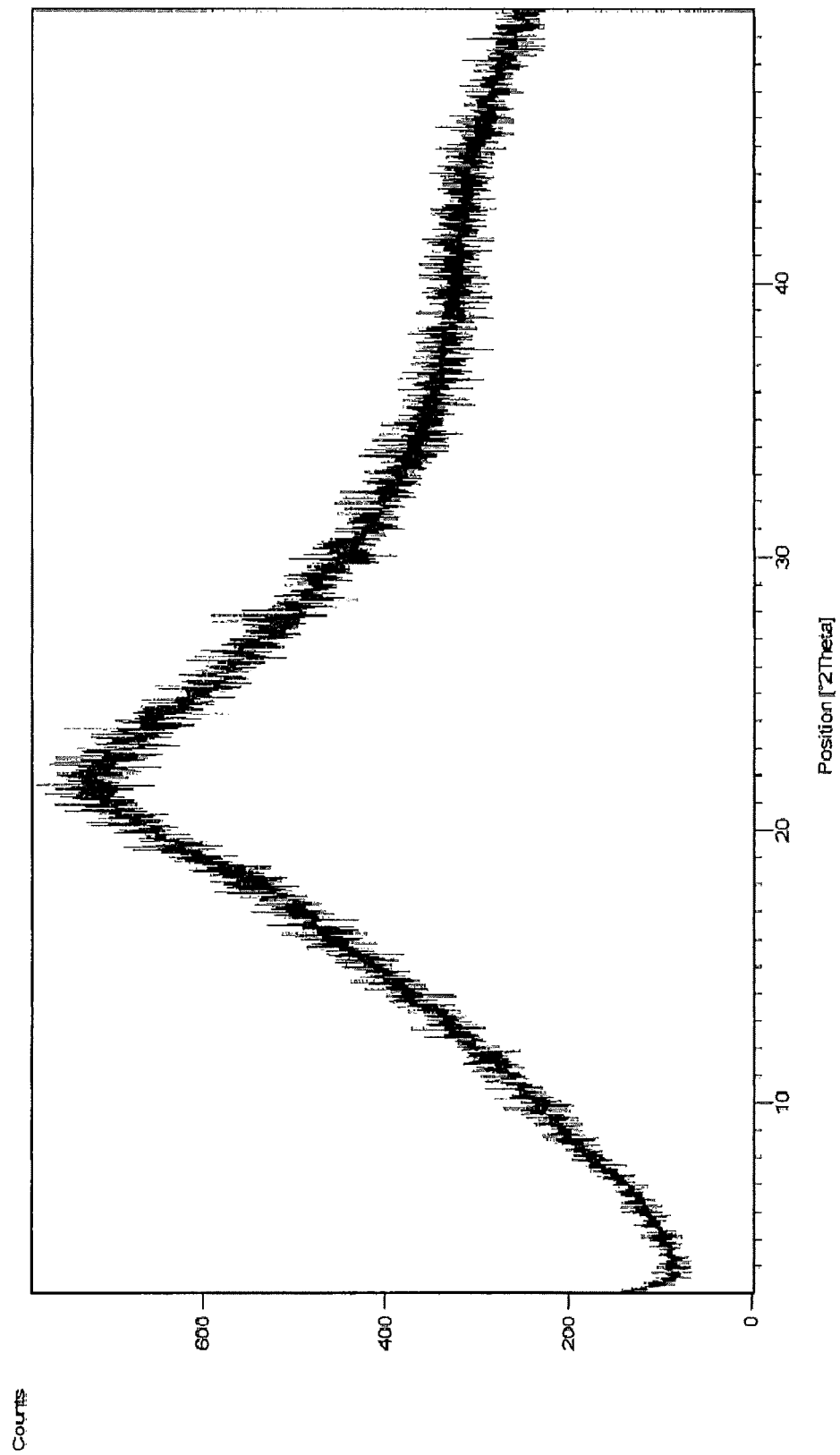
Fig. 16: PXRD pattern of composition of Example 15

PHARMACEUTICAL COMPOSITION

RELATED APPLICATIONS

This application is a National Stage application of PCT/IN2013/000568 filed Sep. 20, 2013, which claims priority to Indian Patent Application No. 2739/MUM/2012 filed Sep. 20, 2012, the entire disclosures of which are hereby incorporated by reference.

FIELD OF THE INVENTION

The present invention relates to a novel pharmaceutical composition having enhanced bioavailability through improved aqueous dissolution of poorly water soluble drugs, and a method for preparing it. The invention more particularly relates to an oral pharmaceutical composition containing active ingredients of poor aqueous solubility, more specifically, antiparasitic and antipneumocystic drug Atovaquone alone or in combination with Proguanil.

BACKGROUND OF THE INVENTION

Numerous pharmaceutical drugs suffer from the disadvantage of being poorly soluble in an aqueous medium, thus having an insufficient dissolution profile to be able to be absorbed in systemic circulation following oral administration, consequently are less bioavailable. In order to achieve sufficient therapeutic effect, the therapeutic dose required to be administered must thus be increased in order to obviate this disadvantage. This particularly applies to compounds classified into Class II according to US biopharmaceutical classification system.

Atovaquone is a well-known antiparasitic and antipneumocystic drug, which is commercially available in different dosage forms and various doses since 1992, but the bioavailability of tablet formulations barely crosses 12% (23% under fat fed conditions) and for oral non-sized suspension bioavailability is about 23% (46-48% under fat fed condition). Indeed, due to its poor hydrosolubility, Atovaquone is poorly absorbed in the digestive tract and consequently its bioavailability is incomplete, irregular and often varies from one person to another. Fat meals help to dissolve the drug in the lipids present in the food. In order to achieve therapeutic levels of atovaquone, patient requires having sufficient fatty food, and most often, it is impractical due to condition/severity of the underlying disease nature.

Atovaquone (Formula I), chemical name being trans-2-[4-(4-chlorophenyl)cyclohexyl]-3-hydroxy-1,4-naphthoquinone, is a hydroxy-1,4-naphthoquinone, an analog of Ubiquinone, with antipneumocystic and anti-malarial activity. It has previously been disclosed, for example, in European Patent No. 1,23,238 and 0675711 that Atovaquone is active (in animals and in vitro) against *Pneumocystis (carinii) jirovecii*, Plasmodia, tachyzoite and cyst forms of *Toxoplasma gondii*, and *Eimeria* spp., a causative agent for Coccidiosis. Further uses of Atovaquone for Cryptosporidiosis and Babesiosis are disclosed in European patent application no. 0496729 and U.S. Pat. No. 5,559,156 respectively.

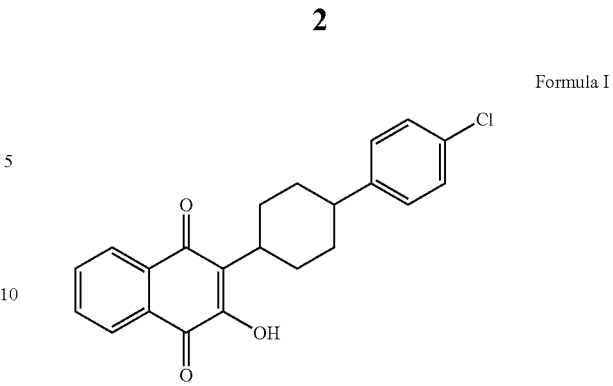

Formula I

For treatment as well as prophylaxis of malaria, proguanil hydrochloride is co-administered with Atovaquone. Chemical structure of Proguanil is given in Formula II.

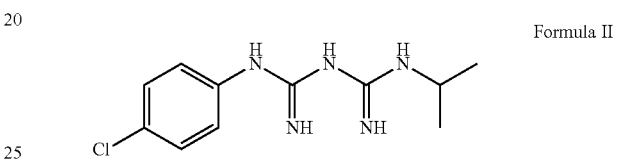

Formula II

Over the past 27 years, nearly 25 million people have died from HIV/AIDS which causes debilitating illness and premature death in people during their prime years of life and has devastated families and communities. The AIDS pandemic and the use of intensive immunosuppressive therapies for a variety of conditions, including before and after organ and tissue transplantation, have established a large population of immunocompromised individuals prone to reactivation of opportunistic pathogens, including *Toxoplasma gondii, Pneumocystis (carinii) jirovecii* and *Eimeria* spp., to name a few of the apicomplexan and non-apicomplexan organisms, particularly in the geographical areas with a high exposure rate to this pathogens. Atovaquone is well known in the art for its use against these pathogenic organisms in normal as well as immunocompromised patients.

Malaria is another infectious disease that causes severe morbidity and mortality with an estimated 300-500 million cases worldwide and more than 1 million deaths annually in sub-Saharan Africa alone and affected patients are of any age group. The disease is caused by another protozoan parasite of the genus *Plasmodium*, transmitted by mosquitoes. The most serious forms of malaria are caused by *Plasmodium falciparum* and *Plasmodium vivax*, but other species (e.g., *Plasmodium ovale, Plasmodium malariae*, and *Plasmodium Knowlesi*) can also infect humans. Control of malaria has been hampered by the spread of drug resistance in both the *Plasmodium* parasites and the *Anopheles* insect vector, and by the lack of an efficacious vaccine (Moorthy, V. S. et al., 2004. Lancet 363:150-156). In order to combat drug resistance and to improve antimalarial chemotherapy, a combination of antimalarials is commonly used, either simultaneously or sequentially. One such combination for the treatment of malaria which has previously been disclosed in WO9412164, U.S. Pat. No. 6,413,993, WO2009001367, and WO2009042960 is Atovaquone and Proguanil as hydrochloride salt (trade name: Malarone).

However, use of Atovaquone either alone or with proguanil, as a first line drug against pathogenic parasitic infectious diseases including malaria is severely hampered by the affordability of treatment due to the hefty price of Atovaquone despite its extreme safety profile, primarily linked to its poor aqueous solubility and thereby bioavailability, consequently very high doses of Atovaquone are required for treatment (Curative dose for malaria is 3 gm divided over three days, and ~1.5-3.0 gm/day for other parasitic infections). There are numerous approaches reported in past for increasing the bioavailability of Atovaquone, however, the success is far from reach to make it as a first-line drug for treatment of pathogenic parasitic infections such as Malaria, especially in the third world.

A commercially successful strategy has been reported in U.S. Pat. Nos. 6,018,080 & 6,649,659 for improving bioavailability of Atovaquone. This patent describes the effect of micronizing Atovaquone together with cellulose carriers to improve Atovaquone solubility and thereby increase its bioavailability. This patent uses microfluidization process for preparing microparticle of 0.1-3 micron size of Atovaquone which can improve Atovaquone bioavailability almost double than solely micronizing the Atovaquone. The process comprises microfluidizing a suspension of atovaquone in a carrier such as HPMC, methylcellulose, etc., similar to preparation of solid dispersions in inert carrier polymers. Yet such microparticles of atovaquone are supplied as suspensions to provide the required daily dose to patients (1750 mg/day), and the bioavailability reaches 23% (with non-fat diet) and 46-48% with fat diet. However, the preparation method in that patent is not completely satisfactory in as much as it does not lead to complete bioavailability of the active ingredient, and suffers from several disadvantages. It should be especially noted that a fat diet alters the bioavailability of the micronized formulation more than double, however, should add wide variability due not only to fat content of the food, but also the capacity of absorption of fat between subjects may vary drastically, and thus therapeutic levels of Atovaquone may not been achieved. A possible reason for resistance to malaria treatment by Atovaquone is also discussed later which is due to this variability in fat dependent absorption and bioavailability. Moreover, the microfluidized microparticles of atovaquone cannot easily be formulated into conventional dosage forms like tablet or capsule as those formulation techniques would not allow to maintain the microparticulate matter, leading to agglomerization/crystallization and thus preferably, it is formulated in suspension, rather than inexpensive Tablet/capsule dosage forms.

Nanosupension for enhanced bioavailability is reported in Antimicrob Agents Chemother. 2001 June; 45(6): 1771-1779, however, this also limits its application to micro/nano liquid suspensions for oral administration, and suffers from the above limitation, when to be used in combination with drugs like proguanil. Atovaquone loaded nanocapsules was reported in International Journal of Pharmaceutics Volume 250, Issue 1, 2 Jan. 2003, Pages 273-281, and oily solutions of atovaquone with pluronic surfactants are reported in Journal of Pharmacy and Pharmacology, Volume 58, 2006, Pages 809-820, however, these approaches suffers from commercial applicability because the drug loading concentration in the oil or polymer carrier were extremely low to formulate convenient dosage forms.

Lipid based nanosuspension dispersions of atovaquone are reported by Borhade et al., in Advances in Technology and Business Potential of New Drug Delivery Systems 2011. Solid dispersion of atovaquone-proguanil was also reported under solvent free process condition (ibid), however, the bioavailability reaches only upto 60%, though the aqueous solubility of the formulation is not disclosed. The success of solid dispersion on a polymer carrier reportedly depends on the nature of polymer and its solubility in aqueous solutions.

US2008248117, however, reports that solid dispersions has a limitation of increasing solubility of the drug particles beyond the aqueous solubility of the polymer carriers used, as the drug particles are of crystalline in nature, and thus when the polymer coating is leached in the aqueous medium, further solubility is limited by the solubility of crystalline compound in the aqueous solution, and thus aims to form solid solutions of poorly water soluble drugs in polymer carriers, wherein amorphous drug particles are embedded on polymer carriers. The process reported in US2008248117, however, is by short heating of an aqueous suspension of poorly water soluble drugs in suitable polymer carrier under high temperature and pressure, followed by rapid drying to form solid solutions. Although this process forms solid solutions with some of the molecules illustrated, characterized to be amorphous under powder X-Ray diffraction, however, a generalization of the process to get solid solution of all poorly soluble drugs is questionable for following reasons: Water is used as a solvent, and the drug must dissolve in aqueous solution at least for a short time at the high temperature and pressure condition to form amorphous, failing which will result in crystalline nature of the drug. The drug must also be able to remain in the amorphous nature, at least during the period of processing, failing which a rapid phase change to crystalline nature may result, and such changes in the nature of the active agent are likely to provide variability in the dissolution rate.

This aspect is further confirmed by the enhancement in the solubility of the drugs tested in US2008248117:

| Product | Resistance to crushing | Release after 15 min in % | Release after 30 min in % |
|---|---|---|---|
| Example 1 | 225 | 62 | 99 |
| Comparative example 1 | 174 | 42 | 80 |
| Theophylline crystals | 140 | 34 | 78 |

| Product | Release after 15 min in % | Release after 30 min in % |
|---|---|---|
| Example 2 | 55 | 101 |
| Comparative example 2 | 35 | 66 |
| Carbamazepine crystals | 22 | 53 |

The results show that the dissolution rates of the tested drugs increase only marginally to either solid dispersion or the crystals of the active drugs, and the best results show that the solubility is doubled in comparison with the crystals of active drug, for example Carbamazepine. The poor aqueous solubility of the solid solutions of US20080248117 may be attributed to microcrystalline nature of the active drug, which is not been able to be characterized by powder X-Ray diffraction, and powder XRD pattern resembles that of amorphous compound primarily due to the interference of amorphous hydrophilic polymer, and thus fails to characterize microcrystalline nature of active drug, but reflects in poor aqueous solubility. And thus this formulation fails to improve the solubility of compounds such as atovaquone significantly. Moreover, Atovaquone is so far not reported to exist in amorphous form, as processes like lyophilization leads to crystalline atovaquone (ref: WO2009007991), therefore the solution formed for a short period and rapid drying, will allow atovaquone to be precipitated in crystalline form.

It is also worth noting that the dissolution media used for atovaquone is 40% isopropanol buffered to pH 8.0 with potassium dihydrogen phosphate, and product dissolution kinetics are measured in a fixed volume of the dissolution medium, agitated by means of a standardized device; however, the use of organic solvents as dissolution medium neither shows the true picture of in-vivo dissolution, nor shows aqueous solubility. Regulatory authorities in all territories strongly discourage the use of organic solvents in in-vitro dissolution experiments for simple reason that they do not reflect a simulation of in-vivo conditions. Probably atovaquone is an exclusive drug which is recommended with use of organic solvents for which any other aqueous physiologically acceptable dissolution medium was failed to show the required drug dissolution.

To improve the dissolution profile of Atovaquone and its bioavailability, thereby reducing the dose requiring to be administered, it would be advantageous to increase its aqueous dissolution so that it could attain a level close to 100%. Since, Atovaquone is known to be a class II drug according to BCS classification, increasing the aqueous dissolution rate may directly yield in increased absorption and bioavailability.

Thus, there is a need to improve Atovaquone bioavailability by attaining, a level close to 100% dissolution in aqueous dissolution medium, thereby greatly influencing pharmacokinetic effects, bioavailability and therapeutic efficacy with minimized Interindividual variability. This forms the object of the present invention.

SUMMARY OF THE INVENTION

Applicants have found that, surprisingly, it is possible to prepare compositions of Atovaquone or its combinations with proguanil having good aqueous solubility and thus enhanced bioavailability. The invention thus provides an aqueous soluble solid oral pharmaceutical composition comprising Atovaquone or its combination with proguanil or atovaquone.proguanil complex or a pharmaceutically acceptable salt, solvate or prodrug thereof having a dissolution of atovaquone at least 20% in 5 minutes, 30% in 10 minutes, 40% in 15 minutes, 50% in 30 minutes and 75% in 45 minutes, as measured using the rotating blade method at 75 rpm in a dissolution medium constituted by water with 2.5% by weight sodium lauryl sulfate or 2% by weight Cremophor/Kolliphor EL.

Thus the aqueous soluble solid oral pharmaceutical composition comprises:
(a) Atovaquone or its combination with proguanil or atovaquone.proguanil complex or a pharmaceutically acceptable salt, solvate or prodrug thereof as active ingredient(s);
(b) At least one hydrophilic polymer, optionally one or more surfactants and/or hydrosoluble carrier(s); and
(c) Optionally inert pharmaceutical excipients.

In one embodiment of the invention, the composition comprises:
(a) the active ingredient(s) in a homogenous phase with a hydrophilic polymer(s), the said hydrophilic polymer is at least 10% by weight of atovaquone or atovaquone.proguanil complex;
(b) optionally one or more surfactants and/or hydrosoluble carriers; and
(c) optional inert pharmaceutical excipients.

In one aspect of the said embodiment, the surfactant is present within the homogenous phase of the active ingredient and the hydrophilic polymer, and in another aspect the surfactant is present outside the homogenous phase.

The suitable hydrophilic polymer(s) is selected from a group consisting of Poly (vinyl pyrrolidone), Poly (vinyl alcohol), Poly (vinyl acetate), Poly (vinyl caprolactum), Poly (ethylene glycol) or a copolymer and/or graft copolymer thereof, preferably a copolymer of Poly (vinyl pyrrolidone) and Poly (vinyl acetate) (for example, Copovidone, Kollidon™ VA64, Plasdone™ S-630 etc.) or a graft copolymer of Poly (vinyl caprolactum), Poly (vinyl acetate) and Poly (ethylene glycol) (for example, Soluplus™).

The composition according to the present invention is prepared by bringing into association the active ingredient(s) with the hydrophilic polymer(s) and/or surfactant(s) and/or hydrosoluble carrier(s) and/or inert pharmaceutical excipients by means of co- or sequentially subjecting the said components to the process of sifting, grinding, milling, mixing, dissolving, spraying or a combination of such processes in such a way that that the resulting composition provides the required dissolution of Atovaquone according to the present invention.

In one aspect, the said homogenous phase of the composition according to the present invention is prepared co- or sequential sifting of active ingredient(s) and the hydrophilic polymer, optionally together with the said surfactant(s) and/or hydrosoluble carrier(s) through appropriate mesh or sieve, blending for suitable time, optionally including further cycles of sifting or blending to achieve the said homogeneity.

In a further aspect, the said homogenous composition according to the present invention is prepared by dissolving active ingredient(s) and the hydrophilic polymer in suitable solvent, and removing the solvent rapidly, such that the drug does not crystallize at the solidification temperature and a homogeneous phase of active ingredient(s) in the hydrophilic polymer is obtained. The said solvent is selected such that at least 5% of drug and hydrophilic polymer is soluble, preferably about 10% of drug and polymer is soluble, more preferably about 15% of both drug and polymer is soluble, and still more preferably about 20% or more of both the active drug and hydrophilic polymer is soluble in the solvent.

BRIEF DESCRIPTION OF THE DRAWINGS

FIG. 1(a) and FIG. 1(b) are a graph of a comparative study of the dissolution profile of Atovaquone from the compositions according to the invention, compared to that of Malarone™, atovaquone proguanil complex and composition prepared according to US20080248117.

FIG. 2 PXRD pattern of composition of Example 1.
FIG. 3 PXRD pattern of composition of Example 2.
FIG. 4 PXRD pattern of composition of Example 3.
FIG. 5 PXRD pattern of composition of Example 4.
FIG. 6 PXRD pattern of composition of Example 5.
FIG. 7 PXRD pattern of composition of Example 6.
FIG. 8 PXRD pattern of composition of Example 7.
FIG. 9 PXRD pattern of composition of Example 8.
FIG. 10 PXRD pattern of composition of Example 9.
FIG. 11 PXRD pattern of composition of Example 10.
FIG. 12 PXRD pattern of composition of Example 11.
FIG. 13 PXRD pattern of composition of Example 12.
FIG. 14 PXRD pattern of composition of Example 13.
FIG. 15 PXRD pattern of composition of Example 14.

FIG. 16 PXRD pattern of composition of Example 15.

DETAILED DESCRIPTION OF THE INVENTION

Unless otherwise specified, all technical and scientific terms used herein have the same meaning as commonly understood by one of ordinary skill in the art, to which this invention belongs. Although any methods and materials similar or equivalent to those described herein can be used in the practice or testing of the present invention, the preferred methods and materials are described. To describe the invention, certain terms are defined herein specifically as follows.

Unless stated to the contrary, any of the words "including," "includes," "comprising," and "comprises" mean "including without limitation" and shall not be construed to limit any general statement that it follows to the specific or similar items or matters immediately following it. Embodiments of the invention are not mutually exclusive, but may be implemented in various combinations. The described embodiments of the invention and the disclosed examples are given for the purpose of illustration rather than limitation of the invention as set forth the appended claims.

The present invention provides an aqueous soluble solid oral pharmaceutical composition comprising Atovaquone or its combination with proguanil or atovaquone.proguanil complex or a pharmaceutically acceptable salt, solvate or prodrug thereof as active ingredient(s) having a dissolution of Atovaquone at least 20% in 5 minutes, 30% in 10 minutes, 40% in 15 minutes, 50% in 30 minutes and 75% in 45 minutes, as measured using the rotating blade method at 75 rpm in a dissolution medium constituted by water with 2.5% by weight sodium lauryl sulfate.

The composition according to the invention comprises:
(a) Atovaquone or its combination with proguanil or atovaquone.proguanil complex or a pharmaceutically acceptable salt, solvate or prodrug thereof as active ingredient(s);
(b) at least one hydrophilic polymer, and optionally one or more surfactants and/or hydrosoluble carrier(s); and
(c) optionally inert pharmaceutical excipients.

The term 'hydrophilic polymer' should be taken to mean any high molecular weight substance (greater, for example, than 300) having sufficient affinity towards water to dissolve therein and form a solution or a gel at least up to 5% by weight. Examples of such polymers are Poly (vinyl pyrrolidone), Poly (vinyl alcohol), Poly (vinyl acetate), Poly (vinyl caprolactum), Poly (ethylene glycol) or a copolymer and/or graft copolymer thereof, preferably a copolymer of Poly (vinyl pyrrolidone) and Poly (vinyl acetate) (for example, Copovidone, Povidone K-30, Kollidon™ VA64, Plasdone™ S-630 etc.) or a graft copolymer of Poly (vinyl caprolactum), Poly (vinyl acetate) and Poly (ethylene glycol) (for example, Soluplus™).

The preferred hydrophilic polymer are Copovidone, a copolymer of Poly (vinyl pyrrolidone) and Poly (vinyl acetate) and Soluplus™, a graft copolymer of Poly (vinyl caprolactum), Poly (vinyl acetate) and Poly (ethylene glycol). The copovidone used in this invention has, for example, a molecular weight between 24000 and 70000, preferably between 45000 and 70000. The caprolactum-vinyl graft co-polymer used according to the invention has, for example, a molecular weight comprised between 90000 and 140000.

Within the context of the invention "hydrosoluble carrier" means any excipient, generally hydrophilic, pharmaceutically inert, crystalline or amorphous, in a particulate form, and which is soluble in an aqueous medium or able to swell in aqueous medium for facilitating the disintegration/dissolution of the hydrophilic polymer-drug matrix. Examples of such excipients are derivatives of sugars, such as sucrose, lactose, saccharose, cellulose derivatives such as Hydroxypropyl cellulose, Hydroxypropylmethyl cellulose, microcrystalline cellulose, corn starch, hydrolyzed starch (maltodextrine), sodium starch glycolate etc. or mixtures, are also suitable.

The term "surfactant" is used in its conventional sense in this invention. Any surfactant is suitable, whether it be amphoteric, non-ionic, cationic or anionic. Examples of such surfactants are: sodium lauryl sulfate, monooleate, monolaurate, monopalmitate, monostearate or another ester of polyoxyethylene sorbitane or polyethylene glycol (such as Gelucire), sodium dioctylsulfosuccinate (DOSS), lecithin, stearylic alcohol, cetostearylic alcohol, cholesterol, hydrogenated castor oil and derivatives or fractions thereof such as polyoxyethylene ricin oil, Cremophor or Kolliphor of different grades such as, Cremophore EL/Kolliphor EL (Macrogolglycerol ricinoleate or Polyoxyl 35 castor oil) and Cremophor or Kolliphor RH-40 (Macrogolglycerol hydroxystearate or Polyoxyl 40 hydrogenated castor oil) hydrogenated polyoxyethylene fatty acid glycerides, pluronic surfactants such as Poloxamer™ of different molecular weights etc. Mixtures of surfactants are also suitable.

In one embodiment of the said invention, the composition comprises:
(a) the active ingredient(s) in a homogenous phase with a hydrophilic polymer(s), the said hydrophilic polymer is at least 10% by weight of atovaquone or atovaquone.proguanil complex;
(b) optionally one or more surfactants and/or hydrosoluble carriers; and
(c) optional inert pharmaceutical excipients.

Within the context of the invention "homogenous" refers to a uniform mixture or phase, at least partially, of the drug and hydrophilic polymer, preferably at least 75% of the drug particles forming the uniform mixture or phase with polymer, preferably 80%, more preferably 90% and even more preferably 100% of active ingredient particles form uniform phase with the polymer employed.

In one aspect of the said embodiment, the homogenous mixture or phase is prepared by co- or sequential sifting of active ingredient(s) and the hydrophilic polymer, optionally together with the said surfactant(s) and/or hydrosoluble carrier(s) through appropriate mesh or sieve, blending for suitable time, optionally including further cycles of sifting or blending to achieve the said homogeneity.

In an another aspect of the embodiment, the homogenous mixture or phase is prepared by dissolving active ingredient(s) and the hydrophilic polymer in suitable solvent, and removing the solvent rapidly, such that the drug does not crystallize at the solidification temperature and a homogeneous phase of active ingredient(s) in the hydrophilic polymer is obtained. The said solvent is selected such that at least 5% of drug and hydrophilic polymer is soluble, preferably about 10% of drug and polymer is soluble, more preferably about 15% of both drug and polymer is soluble, and still more preferably about 20% or more of both the active drug and hydrophilic polymer is soluble in the solvent.

The preferred surfactants are poloxamer, Cremophor/Kolliphor, Gelucire or sodium lauryl sulphate. The surfactants may be, co-precipitated with the polymer matrix and drug. In one embodiment the surfactant is employed outside the pre-formulated homogeneous mixture or phase containing active ingredient(s). In another embodiment the surfactant is a part of the pre-formulated homogeneous mixture or phase containing active ingredient(s).

When the hydrophilic polymer matrix of atovaquone is made in combination with proguanil, within the context of the invention, it includes its free form and proguanil hydrochloride or other pharmaceutically acceptable salts thereof.

The invention further provides a method for preparing a pharmaceutical composition, comprising the steps of bringing into association the active ingredient(s) with the hydrophilic polymers and/or antioxidant(s) and/or surfactants and/or hydrosoluble carriers and/or inert pharmaceutical excipients and shaping the product into the desired dosage form in such a way that the resultant product or dosage form provides a dissolution of Atovaquone at least 20% in 5 minutes, 30% in 10 minutes, 40% in 15 minutes and 75% in 45 minutes, as measured using the rotating blade method at 75 rpm in a dissolution medium constituted by water with 2.5% by weight sodium lauryl sulfate or 2% by weight Cremophor/Kolliphor EL.

The steps of bringing into association the active ingredient(s) with the said components may be carried out by co- or sequentially subjecting the components to sifting, grinding or milling or dissolving into one or more solvents or spraying or mixing or a combination thereof.

In one aspect, the composition of the present invention is prepared by the steps comprising:
(a) co- or sequential sifting of active ingredient(s) and the hydrophilic polymer, optionally together with the said surfactant(s) and/or hydrosoluble carrier(s) through appropriate mesh or sieve;
(b) blending for suitable time, optionally including further cycles of sifting or blending to achieve the desired homogeneity;
(c) optionally subjecting the ingredients of step (b) to granulation, drying and sifting before lubrication for suitable time; and
(d) formulating the material obtained in step b) or c) into a conventional dosage form with optional inert pharmaceutical excipients.

In another aspect, the composition of the present invention is prepared by the steps comprising:
(a) preparing a solution of Active ingredient(s) and hydrophilic polymer in a suitable solvent wherein the concentration of active ingredient and polymer is such that Atovaquone remains in a homogeneous solution at the freezing temperature of the polymer and, optionally adding a surfactant;
(b) removing the solvent by evaporation to form a preformulated powder or granules of atovaquone in the hydrophilic polymer;
(c) optionally mixing said preformulated powder with an inert hydrosoluble carrier;
(d) formulating the material obtained in step b) or c) into a conventional dosage form with optional inert pharmaceutical excipients.

The evaporation of the solvent may be accomplished by conventional techniques such as by spray drying, distillation, evaporation under vacuum, vacuum microfluidization etc. Preferably the solvent is evaporated by spray drying or vacuum evaporation. In case of vacuum evaporation of solvent, the resulting powder or granulate of hydrophilic polymer matrix containing the active drug is isolated or separated from the reactor by addition of a suspending solvent in which the drug and polymer are sparingly soluble, followed by filtering out the particles of hydrophilic polymer matrix containing the active drug and drying.

The method can comprise a step in which products obtained from step (b) or (c) are compressed, with or without additional excipients.

The solvent can be selected from one or more of suitable solvents, preferably the solvent choice is determined by the solubility of both drug & hydrophilic polymer. For example, in case of Atovaquone and co-povidone, suitable solvents include alcoholic solvents such as methanol, ethanol, isopropanol; ketone solvents include, acetone, methylethyl ketone; ester solvents such as including ethyl acetate; ether solvents such as those including tetrahydrofuran; and chlorinated solvents such as those including dichloromethane. More preferably the solvents are selected from methanol, ethanol, ethyl acetate, dichloromethane and acetone.

The use is already known of a polymer, such as polyvinylpyrrolidone or a copolymer of polyvinylpyrrolidone, for producing tablets, in concentrations of the order of 0.5 to 5% by weight, at a maximum 10% by weight. In this case, the polyvinylpyrrolidone is used as a binder.

The use of polymer, such as polyvinylpyrrolidone for manufacturing "solid dispersions" is also known, obtained in general by co-precipitation, co-fusion or liquid-phase mixing followed by drying. Similarly, the use of a caprolactum copolymer such as Soluplus™ is known. Nevertheless, nothing in the state of the art neither teaches nor suggests the present invention.

In one of the embodiments what we have here is a solution of the active ingredient(s) as fluidized amorphous nanoparticulate matter forming a homogeneous phase with polyvinylpyrrolidone carrier, which avoids problems of crystallization of Atovaquone and/or Atovaquone-Proguanil and re-agglomeration of the particles.

The solutions of individual drugs and the hydrophilic polymer may be prepared individually or a solution of all the components may be prepared in a single solvent together, and filtered to remove any undissolved material. When Atovaquone-proguanil complex is prepared separately or in the hydrophilic polymer, an equimolar amount of both the drugs may be employed. The concentration of the individual drug may be adjusted to the proposed treatment regimen when a combination of both drugs employed, for example for a combination of Malarone®, 250 mg Atovaquone and 100 mg of proguanil hydrochloride may be used.

The compositions according to the invention can additionally contain any excipient conventionally used in the pharmaceutical and chemical fields which is compatible with the active ingredient, such as binders, fillers, pigments, disintegrating agents, lubricants, wetting agents, buffers, etc. As examples, excipients able to be used in this invention we can cite: microcrystalline cellulose, lactose, starch, colloidal silica, sodium starch Glycollate, talc, glycerol esters, sodium stearyl fumarate, sodium lauryl sulfate, monooleate, monolaurate, monopalmitate, monostearate or another ester of polyoxyethylene sorbitane or polyethylene glycol (such as Gelucire), sodium dioctylsulfosuccinate (DOSS), lecithin, stearylic alcohol, cetostearylic alcohol, cholesterol, hydrogenated castor oil and derivatives or fractions thereof such as polyoxyethylene ricin oil, Cremophor or Kolliphor of different grades such as, Cremophore EL/Kolliphor EL (Macrogolglycerol ricinoleate or Polyoxyl 35 castor oil) and Cremophor or Kolliphor RH-40 (Macrogolglycerol hydroxystearate or Polyoxyl 40 hydrogenated castor oil) hydrogenated polyoxyethylene fatty acid glycerides, pluronic surfactants such as Poloxamer™ of different molecular weights, titanium dioxide, magnesium stearate, stearic acid, cross-linked polyvinyl pyrrolidone (Crosspovidone), carboxymethyl cellulose, carboxymethyl starch, hydroxypropylcellulose, hydroxymethylcellulose, hydroxypropylmethylcellulose, gelatin, etc.

It is also possible to provide multilayered compositions comprising a layer of hydrophilic polymer containing the active drug and a layer comprising additives, for the manufacture of tablets. In this embodiment, the outer layer comprises a disintegration agent, surfactants, glidants and, for example, a lubricant; thus covered and mixed granules can then be readily compressed that can easily disintegrate in water.

The compositions according to the invention comprise, in general, based on the total composition weight, comprising hydrophilic polymer, active drug and surfactant, excluding the outer phase or layer of additives, the hydrophilic polymer making up from 5% to 95% by weight, preferably 10% to 80% by weight, the Atovaquone and/or Atovaquone-proguanil representing from 5 to 95% by weight, preferably from 10 to 80% by weight, and surfactants may represent about 0-10% by weight. When the composition taken together with hydrophilic carrier and the outer layer, the hydrophilic carrier representing from 10% to 80% by weight, preferably 25% to 45% by weight, the surfactant making up from 0% to 10% by weight, preferably 0.1% to 3% by weight. The outer layer or phase if present, can make up to 0%-80% by weight of the total weight, preferably up to 1%-50% by weight.

More specifically, the weight ratio of active drug(s) to hydrophilic polymer can for example, be comprised between 10:1 to 1:10, preferably, for example between 5:1 to 1:5.

The compositions of the invention are particularly suitable for administering active ingredients by oral route. Pharmaceutical formulations within the scope of the present invention include, for example, discrete solid dosage forms such as boluses, pills, tablets, Capsules, which are preferred formulations and non-discrete dosage forms such as powder or granules.

In one embodiment, the composition according to the invention takes the form of tablets. This tablet results by molding in an inert liquid diluent or preferably by the compression of elements (b) and (c) as such or after granulation.

In another embodiment, the composition of the invention takes the form of powder or granules enclosed inside a capsule, for example in gelatin shell, optionally sealed.

In yet another embodiment, the composition according to the invention is in the form of a powder, granules or a paste, optionally filled in a vial or sachet.

The process according to one of the embodiments of the invention, as has been indicated, comprises spraying or evaporating a solution of an active ingredient and the hydrophilic polymer onto an inert carrier to form powder or granules of homogeneous drug-polymer phase. The obtained powder may be mixed, in a conventional manner, with hydrosoluble carriers, surfactants and other pharmaceutical excipients, compressed into a tablet form or form agglomerates that can be filled into a capsule shell or bag. When the granulate obtained (whether subsequently coated or not) is compressed to form tablets, this step can be implemented using any conventional equipments, known to a skilled artisan.

In yet another embodiment, the invention provides use of the composition according to the invention for the preparation of a medicament useful for the treatment or prophylaxis or both of a protozoal parasitic infection or an infection caused by *Pneumocystis (carinii) jirovecii* in mammals, wherein the protozoal parasitic infection is selected from the group consisting of malaria, *babesia*, cryptosporidiosis, coccidiosis or toxoplasmosis.

EXAMPLES

The following examples illustrate in a non-limiting manner a few compositions according to the invention suitable for different dosage forms:

Example 1

1.0 gm Atovaquone was dissolved in 40 mL Methylene di chloride at 30±2° C. In another flask 5.0 gm Plasdone S-630 was dissolved in 50 mL Methylene di chloride at 30±2° C. to get a clear solution. Both the solutions were filtered and mixed together; the solvent from the mixture was removed by distillation till a residue was obtained. The residue was dried in oven at 55-60° C. under vacuum. The phase homogeneity of the product so obtained was found to be 100% as characterized by PXRD and electron diffraction during transmission electron microscopy.

Example 2

1.0 gm atovaquone was dissolved in 5 mL Tetra hydro furan at 30±2° C. to get clear solution. In another flask 5.0 gm Plasdone S-630 was dissolved in 20 mL Tetra hydro furan at 30±2° C. to get a clear solution. Both the solutions were filtered and mixed; the solvent from the mixed solution was removed by distillation till a residue was obtained. The residue was dried in oven at 55-60° C. under vacuum. The phase homogeneity of the product so obtained was found to be 100% as characterized by PXRD and electron diffraction during transmission electron microscopy.

Example 3

1.0 gm Atovaquone was dissolved in 40 mL Methylene di chloride at 30±2° C. In another flask 5.0 gm Plasdone S-630 was dissolved in 50 mL Methylene di chloride at 30±2° C. to get a clear solution. Both the solutions were filtered and mixed together, the solvent from the mixture was removed by distillation till a residue was obtained. To the residue was added 50 mL Hexane, stirred and filtered to get the solid. It was dried in oven at 55-60° C. under vacuum. The phase homogeneity of the product so obtained was found to be 71.1% as characterized by PXRD.

Example 4

2.0 gm Atovaquone and 10.0 gm Plasdone S-630 was stirred with 70 mL acetone at 56±2° C. to get a clear solution, the solution was filtered and the solvent from the filtered solution was removed by distillation till a residue was obtained. The residue was dried in oven at 55-60° C. under vacuum. The phase homogeneity of the product so obtained was found to be 100% as characterized by PXRD and electron diffraction during transmission electron microscopy.

Example 5

0.5 gm mixture of Atovaquone and Proguanil Hydrochloride (Containing Atovaquone and Proguanil Hydrochloride in 1:1 w/w) was dissolved in mixture of 18 mL Tetra hydro furan and 5 mL methanol. To this a solution of 2.5 gm Plasdone S-630 dissolved in 20 mL Tetra hydro furan was added, stirred, filtered and the solvent was distilled out under vacuum at 40-45° C. to get the solid mass, it was dried in oven at 55-60° C. under vacuum. The phase homogeneity of the product so obtained was found to be 100% as characterized by PXRD and electron diffraction during transmission electron microscopy.

Example 6

0.5 gm mixture of Atovaquone and Proguanil Hydrochloride (Containing Atovaquone and Proguanil Hydrochloride in 2.5:1 w/w) was dissolved in mixture of 20 mL Tetra hydro furan and 8 mL methanol. To this a solution of 2.5 gm Plasdone S-630 dissolved in 20 mL Tetra hydro furan was added, stirred, filtered and the solvent was distilled out under vacuum at 40-45° C. to get the solid mass. It was dried in oven at 55-60° C. under vacuum. The phase homogeneity of the product so obtained was found to be 100% as characterized by PXRD and electron diffraction during transmission electron microscopy.

Example 7

6.8 gm Plasdone S-630 was dissolved in 30 ml ethanol, 2.0 gm Atovaquone and 1.4 gm Proguanil free base was added, 185 ml of ethanol was added and heated to 40-45° C. to get clear solution, the solution was filtered and solvent removed by distillation under vacuum at 40-45° C. to get the solid mass. It was dried in oven at 55-60° C. under vacuum. The phase homogeneity of the product so obtained was found to be 100% as characterized by PXRD and electron diffraction during transmission electron microscopy.

Example 8

12 gm Plasdone S-630 was dissolved in 60 ml ethanol, to this solution 3 gm atovaquone.proguanil complex was added and more of ethanol (150 ml) was added to get a clear solution at 40-45° C., it was filtered and the solvent was distilled out under vacuum at 40-45° C. from the filtrate to get the solid mass. It was dried in oven at 55-60° C. under vacuum. The phase homogeneity of the product so obtained was found to be 100% as characterized by PXRD and electron diffraction during transmission electron microscopy.

Example 9

6 gm Plasdone S-630 was dissolved in 27 ml of Ethanol, to this solution 3 gm atovaquone.proguanil complex was added and more of ethanol (173 ml) was added to get a clear solution at 40-45° C., it was filtered and the solvent was distilled out under vacuum at 40-45° C. from the filtrate to get the solid mass, it was dried in oven at 55-60° C. under vacuum. The phase homogeneity of the product so obtained was found to be 100% as characterized by PXRD and electron diffraction during transmission electron microscopy.

Example 10

4.0 gm atovaquone.proguanil complex was heated with 40 ml Ethanol, to this 2.0 gm Plasdone S-630 dissolved in 10 ml ethanol was added and heated to 40-45° C. and more of Ethanol (160 ml) was added to get the clear solution. It was filtered and the solvent was distilled out under vacuum at 40-45° C. from the filtrate to get the solid dispersion, it was dried in oven at 55-60° C. under vacuum. The phase homogeneity of the product so obtained was found to be 100% as characterized by PXRD and electron diffraction during transmission electron microscopy and electron diffraction during transmission electron microscopy.

Example 11

5.0 gm atovaquone.proguanil complex was heated with 30 ml Ethanol, to this 0.5 gm Plasdone S-630 dissolved in 15 ml ethanol was added and heated to 40-45° C. and more of Ethanol (335 ml) was added to get the clear solution. It was filtered and the solvent was distilled out under vacuum at 40-45° C. from the filtrate to get the solid mass. It was dried in oven at 55-60° C. under vacuum. The phase homogeneity of the product so obtained was found to be 100% as characterized by PXRD and electron diffraction during transmission electron microscopy.

Example 12

6.8 gm Plasdone S-630 was dissolved in 35 ml MDC, to this 2.0 Atovaquone was added and stirred at 30±2° C., then 1.4 gm Proguanil free base was added. When the color of the reaction mixture changed from yellow to reddish, more of MDC was added to get the clear solution, the reaction mass was filtered, the MDC was distilled out, the product obtained was dried in oven at 55-60° C. under vacuum. The phase homogeneity of the product so obtained was found to be 83.8% as characterized by PXRD.

Example 13

5.0 gm atovaquone.proguanil complex was stirred with 100 ml MDC, to this 10.0 gm Plasdone S-630 dissolved in 100 ml MDC was added dropwise at 30±2° C. heated to 40±2° C., more of MDC was then added to get the clear solution. The reaction mass was then filtered and 150 ml n-Heptane added, solvent distilled out at 40° C. under vacuum. 100 ml of n-Heptane added, stirred and distilled out at 40° C. under vacuum. 100 ml of n-Heptane added stirred and filtered, product washed with n-Heptane, dried in oven at 55-60° C. under vacuum. The phase homogeneity of the product so obtained was found to be 92.1% as characterized by PXRD.

Example 14

4.0 gm Plasdone S-630 was added to 24 ml water and then 1.0 gm Atovaquone was added to it. 12 ml more of water added heated to reflux for 2 hrs. Water was removed by distillation under vacuum. The residue obtained was dried in oven at 55-60° C. under vacuum. The phase homogeneity of the product so obtained was found to be 67.8% as characterized by PXRD.

Example 15

5.0 gm atovaquone.proguanil complex, 10 gm Plasdone S-630, 0.5 gm BHT (Butylated hydroxytoluene) and 450 ethanol was stirred at 30±2° C. for half an hour and then heated to 40±2° C. for two and half hour, filtered, ethanol removed by distillation under vacuum. The product obtained was dried at 60±2° C. under vacuum. The phase homogeneity of the product so obtained was found to be 100% as characterized by PXRD and electron diffraction during transmission electron microscopy.

Example 16

Tablet

(A)

| | | |
|---|---|---|
| Atovaquone.proguanil complex | 30 | parts |
| Copovidone | 16 | parts |
| MCC | 15 | parts |
| Crospovidone | 13 | parts |
| Polyplasdone-XL 10 | 6 | parts |
| Colloidal Silica | 1 | part |
| Corn Starch | 10.5 | parts |
| Magnessium Stearate | 0.5 | parts |
| Lactose | 6 | parts |
| Poloxamer 188 | 2.5 | Parts |
| Total | 100 | |

(B)

| | | |
|---|---|---|
| Atovaquone.proguanil complex | 60 | parts |
| MCC | 23 | parts |
| Povidone K30 | 3 | parts |
| Poloxamer 188 | 4 | parts |
| L-HPC LH 21 | 5 | parts |
| Sodium Starch Glycollate | 4 | parts |
| Magnessium stearate | 1 | parts |
| Total | 100 | |

(C)

| | | |
|---|---|---|
| Product of Example 9 | 49 | parts |
| Lactose | 10 | parts |
| Corn Starch | 39 | parts |
| Poloxamer | 2.5 | parts |
| Magnessium Stearate | 0.5 | parts |
| Total | 100 | |

(D)

| | | |
|---|---|---|
| Product of Example 9 | 47 | parts |
| Lactose | 18.5 | parts |
| Corn Starch | 31.5 | parts |
| Poloxamer | 2.5 | parts |
| Magnessium Stearate | 0.5 | parts |
| Total | 100 | |

(E)

| | | |
|---|---|---|
| Product of Example 14 | 50 | parts |
| MCC | 15 | parts |
| Crospovidone | 12 | parts |
| Polyplasdone-XL 10 | 4.7 | parts |
| Colloidal Silica | 1 | part |
| Corn Starch | 10 | parts |
| Magnessium Stearate | 0.3 | parts |
| Lactose | 5 | parts |
| Poloxamer 188 | 2 | Parts |
| Total | 100 | |

(F)
Granular Part

| | | |
|---|---|---|
| Atovaquone.proguanil complex | 33 | parts |
| MCC (Avicel PH101) | 35 | parts |
| Povidone K30 | 1 | part |
| Copovidone (Kollidon VA64) | 2 | parts |
| Poloxamer 188 | 2.5 | parts |
| L-HPC LH 21 | 3 | parts |
| Sodium Starch Glycollate | 4 | parts |
| SLS | 1.5 | parts |

Extragranular Part

| | | |
|---|---|---|
| MCC (Avicel PH101) | 8.5 | parts |
| Sodium Starch Glycollate | 4 | parts |
| Syloid 244 FP | 2 | parts |
| Talc | 2 | parts |
| SLS | 0.5 | parts |
| Magnessium stearate | 1 | part |
| Total | 100 | |

(G)
Granular Part

| | | |
|---|---|---|
| Atovaquone.proguanil complex | 33 | parts |
| MCC (Avicel PH101) | 42 | parts |
| Povidone K30 | 3 | part |
| Poloxamer 188 | 2 | parts |
| L-HPC LH 21 | 3 | parts |
| Sodium Starch Glycollate | 2 | parts |
| SLS | 1 | parts |

Extragranular Part

| | | |
|---|---|---|
| MCC (Avicel PH101) | 6 | parts |
| Sodium Starch Glycollate | 2 | parts |
| Syloid 244 FP | 2 | parts |
| Talc | 2 | parts |
| SLS | 1 | part |
| Magnessium stearate | 1 | part |
| Total | 100 | |

(H)
Granular Part

| | | |
|---|---|---|
| Atovaquone.proguanil complex | 33 | parts |
| MCC (Avicel PH101) | 15 | parts |
| Povidone K30 | 3 | part |
| Poloxamer 188 | 2 | parts |
| L-HPC LH 21 | 3 | parts |
| Sodium Starch Glycollate | 2 | parts |

Extragranular Part

| | | |
|---|---|---|
| MCC (Avicel PH101) | 35 | parts |
| Sodium Starch Glycollate | 2 | parts |
| Syloid 244 FP | 2 | parts |
| Talc | 2 | parts |
| Magnessium stearate | 1 | part |
| Total | 100 | |

Capsule/Sachet (I)

| | | |
|---|---|---|
| Atovaquone.proguanil complex | 72 | parts |
| Copovidone | 18 | parts |
| Polyplasdone XL-10 | 7 | parts |
| Magnessium Stearate | 0.4 | parts |
| Poloxamer 188 | 2.6 | Parts |
| Total | 100 | |

(J)

| | | |
|---|---|---|
| Product of Example 9 | 90 | parts |
| Polyplasdone XL-10 | 7 | parts |
| Magnessium Stearate | 0.4 | parts |
| Poloxamer 188 | 2.6 | Parts |
| Total | 100 | |

(K)

| | | |
|---|---|---|
| Product of Example 9 | 90 | parts |
| Polyplasdone XL-10 | 7 | parts |
| Magnessium Stearate | 0.4 | parts |
| Poloxamer 188 | 2.6 | Parts |
| Total | 100 | |

(L)

| | | |
|---|---|---|
| Product of Example 15 | 50 | parts |
| Sucrose | 20 | parts |
| Lactose | 20 | parts |
| Maize Starch | 10 | parts |
| Total | 100 | |

In Vitro Dissolution Studies

Comparative dissolution study was conducted in various differential dissolution media constituted by water containing 2.5% by weight sodium lauryl sulfate or 2% by weight Cremophor/Kolliphor EL. A Few compositions according to the present invention, Malarone Tablets and atovaquone.proguanil complex were assessed in this comparative dissolution study in above media.

The dissolution was carried out at 37° C. by the USP dissolution tester, Apparatus II (Paddle method) at a rotation rate of 75 rpm. Aliquots each of 10 ml were withdrawn at time intervals of 5, 10, 15, 30, 45 and 60 minutes with syringe and filter through 0.45µ nylon filter paper in to a test tube. Pipette out 5 ml of solution in a 10 ml of volumetric flask and diluted up to the mark with (Acetonitrile:Water (80:20) and analyzed for Atovaquone content using HPLC method.

HPLC Assay Determination

The amount of dissolved Atovaquone was estimated by reverse phase HPLC (Waters Alliance) in a quaternary mode, with a water 2487/2489 detector. The analysis was performed at 220.nm with a Hypersil BDS (250×4.6×5µ). column maintained at 25° C. (column oven) using a mobile phase (Acetonitrile:Water:Methanol:OPA (525:300:175:5) delivered at a flow rate of 3.0.ml/min and following gradient:

CONCLUSION

In vitro dissolution profile of Atovaquone in the differential dissolution media constituted by water containing 2.5% by weight sodium lauryl sulfate or 2% by weight Cremophor/Kolliphor EL clearly show superiority of the composition of the present invention over prior art and already marketed formulations of Atovaquone. Since Atovaquone is a class II biopharmaceutical compound, such an increase in the aqueous solubility of atovaquone from the compositions of the present invention is likely to reflect in the in vivo conditions.

TABLE 1a

| | % Dissolution in Water + 2.5% SLS medium | | | | | |
|---|---|---|---|---|---|---|
| Compositions | 5 min | 10 min | 15 min | 30 min | 45 min | 60 min |
| Malarone Tablet | 8.9 | 15.4 | 18.2 | 18.3 | 19.0 | 19.3 |
| Atovaquone · Proguanil Complex | 38.9 | 45.7 | 49.5 | 48.3 | 47.8 | 48.4 |
| Composition of Example 14 | 0.98 | 2.08 | 3.75 | 12.98 | 8.15 | 11.97 |
| Composition of Example 15 | 62.5 | 77.6 | 86.15 | 83.89 | 77.83 | 75.87 |
| Composition of Example 16 B | 29.2 | 56.4 | 68.9 | 75.3 | 77.9 | 82.5 |
| Composition of Example 16 C | 28.68 | 37.70 | 45.92 | 68.40 | 83.66 | 88.93 |
| Composition of Example 16 D | 42.73 | 51.70 | 62.62 | 85.32 | 93.07 | 98.42 |
| Composition of Example 16 I | 75.8 | 83.5 | 84.0 | 86.6 | 89.4 | 92.6 |

TABLE 1b

| | % Dissolution in Water + 2% Cremophor EL medium | | | | | |
|---|---|---|---|---|---|---|
| Compositions | 5 min | 10 min | 15 min | 30 min | 45 min | 60 min |
| Malarone Tablet | 3.0 | 8.1 | 12.3 | 21.0 | 25.6 | 29.0 |
| Composition of Example 16F | 37.4 | 62.1 | 68.6 | 75.9 | 80.3 | 85.8 |
| Composition of Example 16G | 32.0 | 53.8 | 63.0 | 70.4 | 76.3 | 79.0 |
| Composition of Example 16H | 35.5 | 46.3 | 56.4 | 63.8 | 75.2 | 76.2 |

What is claimed is:

1. An aqueous soluble oral solid pharmaceutical composition comprising:
   1) atovaquone, 2) a pharmaceutically acceptable salt of atovaquone, or 3) a combination of atovaquone or a pharmaceutically acceptable salt of atovaquone with a second pharmaceutical drug substance, as active ingredient(s),
   wherein an aqueous dissolution of the atovaquone present in the composition is at least 20% in 5 minutes, 30% in 10 minutes, 40% in 15 minutes, 50% in 30 minutes and 75% in 45 minutes, as measured using the rotating blade method at 75 rpm in a dissolution medium constituted by water containing 2.5% by weight sodium lauryl sulfate.

2. The aqueous soluble oral solid pharmaceutical composition according to claim 1, comprising:
   (a) atovaquone or its combination with the second pharmaceutical drug substance as active ingredient(s);
   (b) at least one hydrophilic polymer, and optionally one or more surfactants or hydrosoluble carrier(s); and
   (c) one or more pharmaceutical excipients.

3. The aqueous soluble oral solid pharmaceutical composition according to claim 2, wherein the second pharmaceutical drug substance is proguanil or a pharmaceutically acceptable salt, a complex or a prodrug thereof.

4. The aqueous soluble oral solid pharmaceutical composition according to claim 3, wherein the active ingredient(s) is in a homogenous phase with a hydrophilic polymer(s), and
   wherein the homogenous phase optionally includes one or more surfactant(s), and
   wherein the hydrophilic polymer(s) is present in an amount at least 10% by weight of the amount of the atovaquone or the combined amount of the atovaquone and the proguanil.

5. The aqueous soluble oral solid pharmaceutical composition according to claim 4, wherein the phase homogeneity is at least 75% as characterized and quantified by XRPD.

6. The aqueous soluble oral solid pharmaceutical composition according to claim 2, wherein the at least one hydrophilic polymer is selected from a group consisting of poly (vinyl pyrrolidone), poly (vinyl alcohol), poly (vinyl acetate), poly (vinyl caprolactum), poly (ethylene glycol), a copolymer and a graft copolymer thereof, preferably a copolymer of poly (vinyl pyrrolidone) and poly (vinyl acetate) or a graft copolymer or poly (vinyl caprolactum), poly (vinyl acetate) and poly (ethylene glycol).

7. The aqueous soluble oral solid pharmaceutical composition according to claim 2, wherein the one or more surfactants are amphoteric, non-ionic, cationic or anionic surfactant, selected from a group consisting of sodium lauryl sulfate, monoleate, monolaurate, monopalmitate, monostearate or another ester of polyoxyethylene sorbitane, sodium dioctylsulfosuccinate (DOSS), lecithin, stearylic alcohol, cetostearylic alcohol, cholesterol, polyoxyethylene ricin oil, hydrogenated polyoxyethylene fatty acid glycerides, pluronic surfactants, and a mixture thereof.

8. The aqueous soluble oral solid pharmaceutical composition according to claim 3, wherein the composition comprises atovaquone-proguanil or a pharmaceutically acceptable salts, solvates or prodrugs thereof as the active ingredient, a copolymer of poly (vinyl pyrrolidone) and poly (vinyl acetate) as hydrophilic polymer, one or more pluronic surfactants and optionally one or more inert pharmaceutical excipients.

9. A dosage form suitable for oral administration comprising a discrete dosage form or a non-discrete dosage form, comprising a therapeutically effective amount of the composition according to claim 1, wherein the discrete dosage form is selected from one of a bolus, a pill, a tablet, and a capsule, and wherein the non-discrete dosage form comprises a powder or a granule.

10. The dosage form according to claim 9, wherein the discrete dosage form is a tablet prepared by molding in an inert liquid diluents or by compressing into a suitable machine a therapeutically effective amount of the composition according to claim 1 in the form of a powder or granules, the tablets optionally being coated.

11. The dosage form according to claim 9, wherein, the discrete dosage form is a capsule prepared by filling a therapeutically effective amount of the composition according to claim 1 in the form of a powder or granules, the capsule optionally sealed.

12. The dosage form according to claim 9, wherein the non-discrete dosage form is in the form of a powder, granules or a paste comprising a therapeutically effective amount of the composition according to claim 1, optionally filled in a vial or sachet.

13. A method of at least one of treatment and prophylaxis of a protozoal parasitic infection or an infection caused by *Pneumocystis* (*carinii*) *jirovecii* in mammals, comprising the steps of administering the composition of claim 1.

14. The method of claim 13, wherein the protozoal parasitic infection is malaria, babesia, cryptosporidiosis, coccidiosis or toxoplasmosis.

15. The aqueous soluble oral solid pharmaceutical composition according to claim 3, wherein the phase homogeneity is at least 80% as characterized and quantified by XRPD.

16. The aqueous soluble oral solid pharmaceutical composition according to claim 3, wherein the phase homogeneity is at least 90% as characterized and quantified by XRPD.

17. The aqueous soluble oral solid pharmaceutical composition according to claim 3, wherein the phase homogeneity is 100% as characterized and quantified by XRPD.

18. The aqueous soluble oral solid pharmaceutical composition according to claim 7, wherein the pluronic surfactants is poloxamer, and wherein the poloxamer comprises compounds having different molecular weights.

19. The aqueous soluble oral solid pharmaceutical composition according to claim 8, wherein the copolymer of poly (vinyl pyrrolidone) and poly (vinyl acetate) is selected from one of copovidone or kollidon, wherein the one or more pluronic surfactants is polaxamer comprising compounds of different molecular weights, and wherein the optional one or more inert pharmaceutical excipients is selected from one of corn starch, microcrystalline cellulose, crospovidone, or lactose, or a mixture thereof.

* * * * *